US012805339B2

(12) United States Patent
Grell et al.

(10) Patent No.: US 12,805,339 B2
(45) Date of Patent: Nov. 17, 2026

(54) COMPONENT FOR A STRETCHABLE ELECTRONIC DEVICE

(71) Applicant: IMPERIAL COLLEGE INNOVATIONS LIMITED, London (GB)

(72) Inventors: Maximilian Grell, London (GB); Giandrin Barandun, London (GB); Firat Guder, London (GB); Michael Kasimatis, London (GB); Yasin Cotur, London (GB)

(73) Assignee: IMPERIAL COLLEGE INNOVATIONS LIMITED, London (GB)

(*) Notice: Subject to any disclaimer, the term of this patent is extended or adjusted under 35 U.S.C. 154(b) by 868 days.

(21) Appl. No.: 17/439,121

(22) PCT Filed: Mar. 5, 2020

(86) PCT No.: PCT/EP2020/055924
§ 371 (c)(1),
(2) Date: Sep. 14, 2021

(87) PCT Pub. No.: WO2020/182628
PCT Pub. Date: Sep. 17, 2020

(65) Prior Publication Data

US 2022/0157621 A1 May 19, 2022

(30) Foreign Application Priority Data

Mar. 14, 2019 (GR) .............................. 20190100120
May 23, 2019 (GB) ...................................... 1907270

(51) Int. Cl.
*H01L 21/48* (2006.01)
*A61B 5/00* (2006.01)
(Continued)

(52) U.S. Cl.
CPC .......... *H10W 70/092* (2026.01); *A61B 5/683* (2013.01); *H10W 70/662* (2026.01);
(Continued)

(58) Field of Classification Search
CPC . H01L 21/485; H01L 23/145; H01L 23/4985; H01L 23/49872; H01L 24/80;
(Continued)

(56) References Cited

U.S. PATENT DOCUMENTS 10,139,295 B2 * 11/2018 Yu .......................... G01L 1/241
2003/0095263 A1 * 5/2003 Varshneya .......... A61B 5/6892 356/477

(Continued)

FOREIGN PATENT DOCUMENTS

EP 2902293 A2 8/2015
EP 2 902 293 A3 10/2015

OTHER PUBLICATIONS

PCT Written Opinion of the ISA for PCT/EP2020/055924, mailed Jun. 18, 2020, 7 pages.

(Continued)

*Primary Examiner* — Peniel M Gumedzoe
(74) *Attorney, Agent, or Firm* — Husch Blackwell

(57) ABSTRACT

A method of manufacturing a component for a stretchable electronic device comprises providing a silicon wafer comprising a first surface and a second surface; applying a layer of a conductive metal onto at least a portion of the first surface of the silicon wafer; providing a stretchable silicone substrate having a first surface and a second surface; and plasma bonding at least a portion of the second surface of the silicon wafer to at least a portion of the first surface of the stretchable silicone substrate.

23 Claims, 19 Drawing Sheets

(51) Int. Cl.

| | |
|---|---|
| ***H01L 23/00*** | (2006.01) |
| ***H01L 23/14*** | (2006.01) |
| ***H01L 23/498*** | (2006.01) |
| ***H10W 70/05*** | (2026.01) |
| ***H10W 70/66*** | (2026.01) |
| ***H10W 70/67*** | (2026.01) |
| ***H10W 70/695*** | (2026.01) |
| ***H10W 99/00*** | (2026.01) |

(52) U.S. Cl.
CPC ....... *H10W 70/688* (2026.01); *H10W 70/695* (2026.01); *H10W 99/00* (2026.01); *A61B 2562/0261* (2013.01)

(58) Field of Classification Search
CPC ............... H01L 2924/014; A61B 5/683; A61B 2562/014; A61B 2562/0261; H10W 70/092; H10W 70/688; H10W 70/695; H10W 70/662; H10W 99/00
See application file for complete search history.

(56) References Cited

U.S. PATENT DOCUMENTS

| | | | | |
|---|---|---|---|---|
| 2004/0069340 | A1 | 4/2004 | Luch et al. | |
| 2006/0038182 | A1 | 2/2006 | Rogers et al. | |
| 2013/0052394 | A1 | 2/2013 | Lee | |
| 2013/0243655 | A1 | 9/2013 | Li et al. | |
| 2013/0303873 | A1 | 11/2013 | Janos et al. | |
| 2014/0008234 | A1* | 1/2014 | Wei | C25D 7/126 205/91 |
| 2014/0303452 | A1 | 10/2014 | Ghaffari | |
| 2015/0069617 | A1* | 3/2015 | Arora | H01L 23/564 257/773 |
| 2017/0338254 | A1 | 11/2017 | Reit et al. | |
| 2018/0019213 | A1 | 1/2018 | Dias et al. | |
| 2018/0146545 | A1 | 5/2018 | Wang et al. | |
| 2018/0295722 | A1* | 10/2018 | Renshaw | H10K 85/111 |
| 2018/0296875 | A1* | 10/2018 | Christoforou | A61H 1/0288 |

OTHER PUBLICATIONS

PCT ISR for PCT/EP2020/055924, mailed Jun. 18, 2020, 4 pages.

GB Combined Search and Examination Report for GB 1907270.1.1, dated Oct. 4, 2019, 2019, 6 pages.

Cyril Baby Karuthedath et al: "Characterization of Carbon Black Filled PDMS—Composite Membranes for Sensor Applications", Key Engineering Materials, vol. 753, Aug. 1, 2017 (Aug. 1, 2017), pp. 18-27, XP055702904, D0I: 10.4028/www.scientific.net/KEM.753.18.

Gi Seok Jeong et al., "Solderable and electorplatable flexible electronic circuit on a porous stretchable elastomer" Nature Communications, Jul. 31, 2012, 8 pages.

Examination Report for EP 20 711 820.9, mailed Jun. 23, 2025, 9 pages.

Tang KC et al: "Evaluation of bonding between oxygen plasma treated polydimethyl siloxane and passivated silicon",Journal of Physics: Conference Series, Institute of Physics Publishing, Bristol, GB, vol. 34, No. 1, Apr. 1, 2006 (Apr. 1, 2006), pp. 155-161, XP020109597, ISSN: 1742-6596, DOI: 10.1088/1742-6596/34/1/026.

Cyril Baby Karuthedath et al: "Characterization of Carbon Black Filled PDMS-Composite Membranes for Sensor Applications", Key Engineering Materials, vol. 753, Aug. 1, 2017 (Aug. 1, 2017), pp. 18-27, XP055702904, DOI: 10.4028/www.scientific.net/KEM.753.18.

* cited by examiner 1
3
5
1a
40 mm
6
7
3

3a
5
1
Electroplated Cu Layer
1µm
3
3b
2a
[100] Silicon contact
525µm
2

1a
4a
2b
CB-PDMS sensing element
1µm
4
6
PDMS support
3mm
7
4b
3a
Electroplated Cu Layer
3
1
3b
2a
[100] Silicon contact
2

1a
100 µm
2b
4a
CB-PDMS sensing element
6
4
PDMS support
7
4b

1. Samples: Ag 2, 4, 8 min 2. Sample: Unetched

| Strain/ % | $R_D$/ kΩ | $R_2$/ kΩ | $R_1$/ kΩ | Contact contribution $R_D$-$R_1$/ kΩ |
|---|---|---|---|---|
| 0 | 669.7±1.2 | 104.8±3.2 | 564.8±17.5 | 104.8±4.6 |
| 10 | 665.6±0.2 | 99.3±1.1 | 566.2±17.6 | 99.3±4.3 |
| 25 | 675.6±0.3 | 109.1±1.3 | 566.5±17.6 | 109.1±4.8 |

COMPONENT FOR A STRETCHABLE ELECTRONIC DEVICE

RELATED APPLICATIONS

The present application is a National Phase entry of PCT Application No. PCT/EP2020/055924, filed Mar. 5, 2020, which claims priority from Greece Application No. 20190100120, filed Mar. 14, 2019, and Great Britain Application No. 1907270.1, filed May 23, 2019, all of these disclosures being hereby incorporated by reference in their entirety.

FIELD

The present disclosure relates to a method of manufacturing a component for a stretchable electronic device, and to a component for a stretchable electronic device. The disclosure also relates to a stretchable electronic device comprising such a component. A device for measuring chest expansion and deformation rate comprising such a stretchable electronic device and devices for rehabilitation comprising such a stretchable electronic device are also disclosed, along with devices for sweat analysis and gas sensing.

BACKGROUND

Wearable sensors have the potential to revolutionise sports tracking and healthcare by transferring electronics from conventional rigid materials to flexible and stretchable substrates and monolithically integrated systems that possess a high degree of conformability, durability for in-field applications, and accommodate complex morphologies, enabling more natural integration with biological systems and body placement. Applications such as physiological monitoring and skin-mountable sensors require mechanical properties complementing the properties of human and animal motion only given by elastomeric electronic materials. Commercially available harnesses are typically made from textiles including embedded sensors. These show a disconformity which makes them wearable only for a few days and only during waking hours. On the other hand, elastomeric sensors are usually softer and comfortable enough for frequent and prolonged use. Their elastic modulus can be carefully tuned, which makes devices created from elastomeric materials extremely comfortable and suitable for commercial applications.

In modern global healthcare systems, there is thus a growing demand for stretchable and soft electronic devices, in particular, for flexible and stretchable sensing elements. The emerging field of stretchable sensors and electronics has found a wide range of applications in mechanical, chemical and biological sensing, piezoelectric generators, and photovoltaics. Stretchable devices can conform to curved surfaces, such as the human body, and can instantly adapt to dynamic changes in the geometry of the object they are attached to. Hence, stretchable devices are exceptionally suitable as wearable devices for physiological monitoring and rehabilitation, for example.

Conductive silicone composites are ideal materials for stretchable wearable electronics and they have already been used to develop strain sensors, complementary circuits, energy producing and energy storing elements. However, the development of a reliable interface between conductive silicone composites (soft electronic elements) and conventional inelastic electronics (hard electronic elements), such as wiring and integrated circuits, is a challenge. In particular, one challenge is to provide a mechanically reliable interface between stretchable electronic elements and conventional inelastic electronics which can withstand the stresses and strains experienced by stretchable electronic elements. In particular, another challenge is to provide reliable interfacial adhesion between the composite silicone elastomer elements and hard electronic elements, by overcoming the problem of the chemical inertness of silicones.

Brittle conductive adhesives provide a poor and unreliable mechanical interface between soft electronic elements and hard electronic elements, and are able to withstand only small amounts of stress or strain while maintaining their electrical properties reliably. Such adhesives, for example silver-based conductive epoxy (AgEpoxy), are susceptible to cracking, debonding from silicone-based strain sensors, and eventual failure when strained by as little as 10%. For example, this is because AgEpoxy is brittle, and wetting of silicone by AgEpoxy is poor. Furthermore, silicones bond weakly with most adhesives, due to the low surface energy of silicones.

Additionally, large solid mechanical connections, such as clamps and clasps, as an interface between soft electronic elements and hard electronic elements, are not suitable for miniaturised devices.

Existing metallic contacts may be susceptible to delamination and failure, especially in applications such as physiological monitoring, where the contacts may experience high levels of applied stress and high rates of strain, for example, greater than 2 mm/second.

Jeong, G. S.; Baek, D.-H.; Jung, H. C.; Song, J. H.; Moon, J. H.; Hong, S. W.; Kim, I. Y.; Lee, S.-H. Solderable and Electroplatable Flexible Electronic Circuit on a Porous Stretchable Elastomer. Nat. Commun. 2012, 3 (1), 977, describes a method for fabricating flexible and stretchable electronic devices using a porous elastomeric substrate. Pressurized steam was applied to an uncured polydimethylsiloxane layer for the simple and cost-effective production of porous structure. An electroplated nickel anchor had a key role in bonding commercial electronic components on elastomers by soldering techniques, and metals could be stably patterned and electroplated for practical uses. The proposed technology was applied to develop a plaster electrocardiogram dry electrode and multi-channel microelectrodes that could be used as a long-term wearable biosignal monitor and for brain signal monitoring, respectively.

US2017338254 describes flexible electronics stacks and methods of use. An example flexible electronics stack includes a flexible polymeric substrate film and a rigid inorganic electronic component. The flexible polymeric substrate film includes a thermoset polymer prepared by curing a monomer solution; wherein the monomer solution comprises about 25 wt % to about 65 wt % of one or more thiol monomers and from about 25 wt % to about 65 wt % of one or more co-monomers.

US2004069340 describes deposition of thin film photovoltaic junctions on metal substrates which can be heat treated following deposition in a continuous fashion without deterioration of the metal support structure. In a separate operation an interconnection substrate structure is produced in a continuous roll-to-roll fashion. In this way the interconnection substrate structure can be uniquely formulated from polymer-based materials since it does not have to endure high temperature exposure. Cells comprising the metal foil supported photovoltaic junctions are then laminated to the interconnection substrate structure. Conductive interconnections are deposited to complete the array. The conductive interconnections can be accomplished with a separately prepared interconnection component. The interconnected array is produced using continuous roll-to-roll processing which avoids the need to use the expensive and intricate material removal operations currently taught in the art to achieve electrical interconnections among arrays of photovoltaic cells.

US2006038182 describes methods and devices for fabricating printable semiconductor elements and assembling printable semiconductor elements onto substrate surfaces. The methods, devices and device components are capable of generating a wide range of flexible electronic and optoelectronic devices and arrays of devices on substrates comprising polymeric materials. Also described are stretchable semiconductor structures and stretchable electronic devices capable of good performance in stretched configurations.

US2018146545 describes compositions, devices, systems and fabrication methods for stretchable composite materials and stretchable electronics devices. In some aspects, an elastic composite material for a stretchable electronics device includes a first material having a particular electrical, mechanical or optical property; and a multi-block copolymer configured to form a hyperelastic binder that creates contact between the first material and the multi-block copolymer, in which the elastic composite material is structured to stretch at least 500% in at least one direction of the material and to exhibit the particular electrical, mechanical or optical property imparted from the first material. In some aspects, the stretchable electronics device includes a stretchable battery, biofuel cell, sensor, supercapacitor or other device able to be mounted to skin, clothing or other surface of a user or object.

US2018019213 describes a microelectronic device and methods for forming a microelectronic device. In an embodiment, the microelectronic device includes a semiconductor die that has one or more die contacts that are each electrically coupled to a contact pad by a conductive trace. The semiconductor die may have a first elastic modulus. The microelectronic device may also include an encapsulation layer over the semiconductor die and the conductive trace. The encapsulation layer may have a second elastic modulus that is less than the first elastic modulus. The microelectronic device may also include a first strain redistribution layer within the encapsulation layer. The first strain redistribution layer may have a footprint that covers the semiconductor die and a portion of the conductive traces. The strain redistribution layer may have a third elastic modulus that is less than the first elastic modulus and greater than the second elastic modulus.

Xu, S.; Zhang, Y.; Jia, L.; Mathewson, K. E.; Jang, K.-I.; Kim, J.; Fu, H.; Huang, X.; Chava, P.; Wang, R.; et al. Soft Microfluidic Assemblies of Sensors, Circuits, and Radios for the Skin. Science 2014, 344 (6179), 70-74, describes experimental and theoretical approaches for using ideas in soft microfluidics, structured adhesive surfaces, and controlled mechanical buckling to achieve ultralow modulus, highly stretchable systems that incorporate assemblies of high-modulus, rigid, state-of-the-art functional elements. The outcome is a thin, conformable device technology that can softly laminate onto the surface of the skin to enable advanced, multifunctional operation for physiological monitoring in a wireless mode.

The present disclosure seeks to alleviate, at least to a certain degree, the problems and/or address at least to a certain extent, the difficulties associated with the prior art.

SUMMARY

According to a first aspect of the disclosure, there is provided a method of manufacturing a component for a stretchable electronic device, comprising:

providing a silicon wafer comprising a first surface and a second surface;

applying a layer of a conductive metal onto at least a portion of the first surface of the silicon wafer;

providing a stretchable silicone substrate having a first surface and a second surface; and plasma bonding at least a portion of the second surface of the silicon wafer to at least a portion of the first surface of the stretchable silicone substrate.

Such a method advantageously provides a means to bond silicones to stretchable electronics, and may also provide a component with significantly reduced complexity, reduced manufacturing time, lower operational costs, improved miniaturisation, improved versatility, improved applicability, improved imperceptibility, reduced weight, and reduced manufacturing cost.

In addition, such a method advantageously provides a component having improved adhesion force between hard and soft electronics in a strain sensing system. In particular, such a method may provide a component having increased mechanical strength, durability and reliability. More particularly, such a method may provide a component that can withstand large stresses and/or strains and that is thus suitable for use in a wearable device, where reliability under fast strain rates and tensile forces is essential.

Advantageously, such a method may provide a component for a stretchable electronic device which has reliable interfacial adhesion between soft stretchable electronic elements (such as the stretchable silicone substrate) and conventional inelastic hard electronics. Plasma bonding the silicon wafer to the stretchable silicone substrate exploits the chemistry of silicon and silicone and provides a reliable interface by covalent bonding.

Such a method may also advantageously provide for a simple fabrication process for manufacturing a component for a stretchable electronic device, in that the component can be manufactured in a standard laboratory environment, i.e. without the need for advanced facilities such as a clean room. Such a method is therefore suitable for large scale manufacturing under normal conditions.

Additionally, such a method advantageously may provide for creating solderable, mechanically robust, electrical contacts to interface silicone-based strain sensors with conventional solid-state (hard) electronics.

Plasma bonding at least a portion of the second surface of the silicon wafer to at least a portion of the first surface of the stretchable silicone substrate provides for covalent and conformal adhesion between the silicon wafer and the stretchable silicone substrate. Advantageously, this may provide for a strong and reliable bond between the silicon wafer and the stretchable silicone substrate. In addition, advantageously, the stretchable silicone substrate may remain stretchable even after being bonded to the silicon wafer.

In addition, such a method advantageously provides for a component that has improved elasticity.

Furthermore, such a method advantageously provides for a component with improved interfacial adhesion such that the component may fail in an abrupt manner rather than in a gradual manner. For example, when the component is used in a stretchable electronic device configured to measure a signal, if one or more of the interface between the layer of a conductive metal and the silicon wafer or the interface between the silicon wafer and the stretchable silicone substrate fails, the loss of signal from the stretchable electronic device is abrupt rather than gradually decreasing. This is advantageous so that a user may be able to readily realise with increased certainty and/or obviousness when a stretchable electronic device has failed.

Additionally, such a method may provide for the monolithic integration of electronic components and data-transmission elements with a stretchable electronic device, which enables improves reliability, miniaturisation and simplification of a stretchable electronic device. Furthermore, the integration of such electronic components with the stretchable silicone substrate may provide for decreased size, decreased weight and improved mass production of a component for a stretchable electronic device. Such a component may also provide for a comfortable and imperceptible wearable sensor, user-friendly remote tracking, and personal healthcare control.

Optionally, the method further comprises etching at least a portion of the first surface of the silicon wafer before the step of attaching the layer of a conductive metal onto at least a portion of the first surface of the silicon wafer.

Advantageously, etching at least a portion of the first surface of the silicon wafer provides for increased surface contact adhesion between the silicon wafer and the layer of a conductive metal. This advantageously enables soldering to take place on the component. Furthermore, etching at least a portion of the first surface of the silicon wafer may also provide for a reduction or even a complete elimination of the need to have an interfacial layer between the silicon wafer and the layer of a conductive metal.

Optionally, at least a portion of the first surface of the silicon wafer is nanoporous. This nanoporous surface may be formed through the etching process.

Optionally, the silicon wafer comprises crystalline silicon. The silicon may be p-type silicon or n-type silicon. The doping level of the silicon may be chosen to optimise the conductivity of the silicon, based on the intended application/use of the component.

Optionally, the step of etching at least a portion of the first surface of the silicon wafer before the step of attaching the layer of a conductive metal onto at least a portion of the first surface of the silicon wafer comprises etching at least a portion of the first surface of the silicon wafer such that at least a portion of the first surface of the silicon wafer comprises a rough morphology. Optionally, the rough morphology is nanoporous such that at least a portion of the first surface of the silicon wafer comprises a plurality of nanopores.

Optionally, the step of etching at least a portion of the first surface of the silicon wafer comprises metal-assisted chemical etching.

Optionally, the step of etching at least a portion of the first surface of the silicon wafer comprises etching using a solution comprising $H_2O_2$ and hydrogen fluoride.

Optionally, the method further comprises plating silver electrolessly onto at least a portion of the first surface of the silicon wafer before etching at least a portion of the first surface of the silicon wafer.

Advantageously, plating silver onto at least a portion of the first surface of the silicon wafer before etching said surface serves to assist the etching process.

Optionally, the method further comprises protecting the second surface of the silicon wafer with a protective layer before etching at least a portion of the first surface of the silicon wafer, such that the second surface of the silicon wafer is protected from the etching process.

Optionally, the protective layer comprises a polyimide sheet, polypropylene, Teflon, or one or more other hydrogen fluoride resistant polymers.

Advantageously, protecting the second surface of the silicon wafer protects said surface to preserve an atomically flat surface ideal for conformal plasma bonding.

Optionally, the conductive metal comprises one or more of copper, gold, nickel, cadmium, rhodium, platinum, silver and zinc.

Optionally, the step of attaching a layer of a conductive metal onto at least a portion of the first surface of the silicon wafer comprises electroplating.

Optionally, at least a portion of the stretchable silicone substrate comprises a plurality of conductive particle fillers and/or one or more conductive liquids dispersed in a silicone polymer matrix.

Advantageously, such a method may provide a component for a stretchable electronic device having a stretchable silicone substrate that has improved long-term chemical and mechanical stability, and a low cost. Furthermore, such a method may provide a component for a stretchable electronic device having a stretchable silicone substrate with tunable mechanical and/or electrical properties.

Optionally, at least a portion of the stretchable silicone substrate comprises a plurality of conductive particle fillers, wherein each conductive particle filler may have a size of approximately 50 nm.

Optionally, the stretchable silicone substrate comprises a first layer and a second layer, the first layer of the stretchable silicone substrate comprising the first surface of the stretchable silicone substrate, and the second layer of the stretchable silicone substrate comprising the second surface of the stretchable silicone substrate, wherein the first layer of the stretchable silicone substrate comprises a plurality of conductive particle fillers and/or one or more conductive liquids dispersed in a silicone polymer matrix.

Optionally, the first layer of the stretchable silicone substrate comprises carbon black-filled polydimethylsiloxane (CB-PDMS) and/or gold or silver nanowires and/or single, multiple walled, modified or unmodified carbon nanotubes. Optionally, the second layer of the stretchable silicone substrate comprises polydimethylsiloxane (PDMS) and/or silicone rubber and/or platinum-catalysed silicone (e.g. Ecoflex 10/30/50 or Dragon Skin 10/30/50).

Optionally, the first layer of the stretchable silicone substrate comprises carbon black-filled polydimethylsiloxane (CB-PDMS) and/or the second layer of the stretchable silicone substrate comprises polydimethylsiloxane (PDMS).

Advantageously, polydimethylsiloxane (PDMS) provides for reduced cost and ease of manufacture of the component.

Optionally, the carbon black has a concentration of between 5% to 20% in the polydimethylsiloxane (PDMS) in the first layer of the stretchable silicone substrate.

Advantageously, such a carbon black concentration may provide an optimum electrical resistance in the first layer of the stretchable silicone substrate.

Advantageously, such a carbon black concentration may balance the effects of conductivity of the first layer of the stretchable silicone substrate increasing with increasing carbon black content, with the agglomeration of carbon black (CB) particles on the surface of the first layer of the stretchable silicone substrate. Advantageously, this may prevent modulus mismatch between the first layer of the stretchable silicone substrate and the second layer of the stretchable silicone substrate which may provide robustness in mechanical performance and eliminate delamination and tearing of the first layer of the stretchable silicone substrate as well as the interface between the first layer of the stretchable silicone substrate and the second layer of the stretchable silicone substrate.

Optionally, the carbon black has a concentration of approximately 12% in the polydimethylsiloxane (PDMS) in the first layer of the stretchable silicone substrate.

Advantageously, such a carbon black concentration may provide a low electrical resistance in the first layer of the stretchable silicone substrate, when the component is configured to operate with a 3.3V and/or 5V circuit. Further, such a carbon black concentration may also provide high binding strength.

Optionally, the second layer of the stretchable silicone substrate has a thickness that is greater than a thickness of the first layer of the stretchable silicone substrate.

Optionally, the second layer of the stretchable silicone substrate has a thickness of approximately 3 mm, and the first layer of the stretchable silicone substrate has a thickness of between 1 μm to 0.3 mm.

Optionally, the step of providing a stretchable silicone substrate comprises printing the first layer of the stretchable silicone substrate on top of at least a portion of the second layer of the stretchable silicone substrate, and subsequently curing the first layer of the stretchable silicone substrate and the second layer of the stretchable silicone substrate.

Optionally, the step of curing the first layer of the stretchable silicone substrate and the second layer of the stretchable silicone substrate comprises a curing time of less than or equal to one hour and/or a curing temperature of less than or equal to 150 degrees centigrade.

Optionally, the step of curing the first layer of the stretchable silicone substrate and the second layer of the stretchable silicone substrate comprises a curing time of less than or equal to 48 hours and a curing temperature of approximately room temperature.

Advantageously, a curing time of less than one hour may provide for reduced particle transfer of the plurality of conductive particle fillers and/or one or more conductive liquids from the first layer of the stretchable silicone substrate to the second layer of the stretchable silicone substrate, which would otherwise disrupt the percolation network and lower the conductivity of the first layer of the stretchable silicone substrate.

Advantageously, a curing temperature of less than 150 degrees centigrade enables the plurality of conductive particle fillers and/or one or more conductive liquids in the first layer of the stretchable silicone substrate to establish good contact prior to gelation.

Optionally, the method further comprises soldering one or more electronic components onto the layer of a conductive metal.

Advantageously, such a method provides a component for a stretchable electronic device which has reliable interfacial adhesion between the stretchable silicone substrate and the one or more electronic components. Furthermore, such a method provides a component with an improved tensile strength in contact adhesion between the stretchable silicone substrate and the one or more electronic components.

Advantageously, soldering one or more electronic components to the conductive metal layer provides for the formation of irreversible bonding by metal alloying between the one or more electronic components and the conductive metal layer. Furthermore, advantageously, using soldering in the manufacturing process is minimally disruptive to large scale production.

Optionally, the one or more electronic components comprises one or more wires, integrated circuits, resistors, capacitors, microcontrollers, and/or other solid-state electronic components.

Optionally, the step of soldering comprises tin soldering. Optionally, the tin soldering includes tin-silver-copper (SAC), tin-silver, tin-copper, tin-silver-antimony, tin-antimony and/or tin-bismuth solder, and/or any other low temperature solder.

Optionally, the one or more electronic components are soldered onto the layer of a conductive metal after the layer of a conductive metal has been applied onto at least a portion of the first surface of the silicon wafer, and before at least a portion of the second surface of the silicon wafer is plasma bonded to at least a portion of the first surface of the stretchable silicone substrate.

Optionally, the step of plasma bonding at least a portion of the second surface of the silicon wafer to at least a portion of the first surface of the stretchable silicone substrate comprises treating at least a portion of the second surface of the silicon wafer and at least a portion of the first surface of the stretchable silicone substrate in 100% O2 plasma for an operating time of approximately 35 seconds.

Advantageously, treating said surfaces in 100% O2 plasma activates the bonding surfaces by generation of a silicon oxide layer.

Optionally, the step of plasma bonding at least a portion of the second surface of the silicon wafer to at least a portion of the first surface of the stretchable silicone substrate further comprises providing conformal contact between at least a portion of the second surface of the silicon wafer and at least a portion of the first surface of the stretchable silicone substrate and applying pressure to at least a portion of the second surface of the silicon wafer and at least a portion of the first surface of the stretchable silicone substrate for approximately 30 seconds.

Advantageously, applying pressure to at least a portion of the second surface of the silicon wafer and at least a portion of the first surface of the stretchable silicone substrate has the effect of bringing said surfaces into as best contact as possible. Advantageously, this may remove/avoid air bubbles.

Optionally, the step of plasma bonding at least a portion of the second surface of the silicon wafer to at least a portion of the first surface of the stretchable silicone substrate comprises providing a mask to the first surface of the stretchable silicone substrate such that only one or more predetermined areas of the first surface of the stretchable silicone substrate are plasma bonded to at least a portion of the second surface of the silicon wafer.

Advantageously, using a mask to expose only predetermined areas of the first surface of the stretchable silicone substrate during plasma bonding prevents siloxane cross-linking from occurring on the first surface of the stretchable silicone substrate after the plasma bonding, which would undesirably make the first surface of the stretchable silicone substrate locally more brittle.

Optionally, the mask comprises a polymer film.

Optionally, the method further comprises leaving the silicon wafer and the stretchable silicone substrate to stabilise at room temperature for approximately 3 days, after the step of plasma bonding at least a portion of the second surface of the silicon wafer to at least a portion of the first surface of the stretchable silicone substrate.

Optionally, the method further comprises cleaning at least a portion of the second surface of the silicon wafer and at least a portion of the first surface of the stretchable silicone substrate, using acetone, before at least a portion of the second surface of the silicon wafer is plasma bonded to at least a portion of the first surface of the stretchable silicone substrate.

According to a second aspect of the disclosure, there is provided a component for a stretchable electronic device, comprising:

a silicon wafer comprising a first surface and a second surface;

a conductive metal layer applied to at least a portion of the first surface of the silicon wafer; and a stretchable silicone substrate having a first surface and a second surface, wherein at least a portion of the first surface of the stretchable silicone substrate is covalently bonded to at least a portion of the second surface of the silicon wafer.

Such a component may advantageously have significantly reduced complexity, reduced manufacturing time, lower operational costs, improved miniaturisation, improved versatility, improved applicability, improved imperceptibility, reduced weight, and reduced manufacturing cost.

In addition, such a component advantageously may provide for improved adhesion force between hard and soft electronics in a strain sensing system. In particular, such a component may have increased mechanical strength, durability and reliability. More particularly, such a component may withstand large stresses and/or strains and is thus suitable for use in a wearable device, where reliability under fast strain rates and tensile forces is essential.

Advantageously, such a component may provide for reliable interfacial adhesion between soft stretchable electronic elements (such as the stretchable silicone substrate) and conventional inelastic hard electronics.

Such a component may also advantageously be manufactured in a standard laboratory environment, i.e. without the need for advanced facilities such as a clean room. Such a component may therefore be suitable for large scale manufacturing under normal conditions.

Additionally, such a component provides for creating solderable, mechanically robust, electrical contacts to interface silicone-based strain sensors with conventional solid-state (hard) electronics.

Plasma bonding at least a portion of the second surface of the silicon wafer to at least a portion of the first surface of the stretchable silicone substrate provides for covalent and conformal adhesion between the silicon wafer and the stretchable silicone substrate. Advantageously, this may provide for a strong and reliable bond between the silicon wafer and the stretchable silicone substrate. In addition, advantageously, the stretchable silicone substrate remains stretchable even after being bonded to the silicon wafer.

In addition, such a component advantageously has improved elasticity.

Furthermore, such a component advantageously may have improved interfacial adhesion such that the component may fail in an abrupt manner rather than in a gradual manner. For example, when the component is used in a stretchable electronic device configured to measure a signal, if one or more of the interface between the layer of a conductive metal and the silicon wafer or the interface between the silicon wafer and the stretchable silicone substrate fails, the loss of signal from the stretchable electronic device is abrupt rather than gradually decreasing. This is advantageous so that a user may be able to readily realise with increased certainty and/or obviousness when a stretchable electronic device has failed.

Additionally, such a component may provide for the monolithic integration of electronic components and data-transmission elements with a stretchable electronic device, which enables improves reliability, miniaturisation and simplification of a stretchable electronic device. Furthermore, the integration of such electronic components with the stretchable silicone substrate may provide for decreased size, decreased weight and improved mass production of a component for a stretchable electronic device. Such a component may also provide for a comfortable and imperceptible wearable sensor, user-friendly remote tracking, and personal healthcare control.

Optionally, the silicon wafer comprises crystalline silicon. The silicon may be p-type silicon or n-type silicon. The doping level of the silicon may be chosen to optimise the conductivity of the silicon, based on the intended application/use of the component.

Optionally, the conductive metal later is applied to at least a portion of the first surface of the silicon wafer by electroplating.

Optionally, the conductive metal layer comprises one or more of copper, gold, nickel, cadmium, rhodium, platinum, silver and zinc.

Optionally, at least a portion of the stretchable silicone substrate comprises a plurality of conductive particle fillers and/or one or more conductive liquids dispersed in a silicone polymer matrix.

Advantageously, such a component may have improved long-term chemical and mechanical stability, and a low cost. Furthermore, such a stretchable silicone substrate may have tunable mechanical and/or electrical properties, and sensitivity.

Optionally, at least a portion of the stretchable silicone substrate comprises a plurality of conductive particle fillers, wherein each conductive particle filler may have a size of approximately 50 nm in at least one direction/dimension of each conductive particle filler. For example, each conductive particle filler may comprise a nanowire with a length of approximately 2 mm and a thickness/diameter or approximately 50 nm.

Optionally, the stretchable silicone substrate comprises a first layer and a second layer, the first layer of the stretchable silicone substrate comprising the first surface of the stretchable silicone substrate, and the second layer of the stretchable silicone substrate comprising the second surface of the stretchable silicone substrate, wherein the first layer of the stretchable silicone substrate comprises a plurality of conductive particle fillers and/or one or more conductive liquids dispersed in a silicone polymer matrix.

Optionally, the first layer of the stretchable silicone substrate comprises carbon black-filled polydimethylsiloxane (CB-PDMS) and/or gold or silver nanowires and/or single, multiple walled, modified or unmodified carbon nanotubes, and the second layer of the stretchable silicone substrate comprises polydimethylsiloxane (PDMS) and/or silicone rubber and/or platinum-catalysed silicone (e.g. Ecoflex 10/30/50 or Dragon Skin 10/30/50).

Advantageously, polydimethylsiloxane (PDMS) provides for reduced cost and ease of manufacture of the component.

Optionally, the carbon black has a concentration of between 5% to 20% in the polydimethylsiloxane (PDMS) in the first layer of the stretchable silicone substrate.

Advantageously, such a carbon black concentration may provide an optimum electrical resistance in the first layer of the stretchable silicone substrate.

Advantageously, such a carbon black concentration may balance the effects of conductivity of the first layer of the stretchable silicone substrate increasing with increasing carbon black content, with the agglomeration of carbon black (CB) particles on the surface of the first layer of the stretchable silicone substrate. Advantageously, this prevents a reduction in the adhesive interaction of polydimethylsiloxane (PDMS) with carbon black (CB).

Optionally, the carbon black has a concentration of approximately 12% in the polydimethylsiloxane (PDMS) in the first layer of the stretchable silicone substrate.

Advantageously, such a carbon black concentration may provide a low electrical resistance in the first layer of the stretchable silicone substrate, when the component is configured to operate with a 3.3V and/or 5V circuit. Further, such a carbon black concentration may also provide high binding strength.

Optionally, the second layer of the stretchable silicone substrate has a thickness that is greater than a thickness of the first layer of the stretchable silicone substrate.

Optionally, the second layer of the stretchable silicone substrate has a thickness of approximately 3 mm, and the first layer of the stretchable silicone substrate has a thickness of between 1 μm to 0.3 mm.

Optionally, at least a portion of the first surface of the stretchable silicone substrate is plasma bonded to at least a portion of the second surface of the silicon wafer, such that at least a portion of the first surface of the stretchable silicone substrate is covalently bonded to at least a portion of the second surface of the silicon wafer.

Optionally, the component according to the second aspect of the disclosure may be manufactured using a method according to the first aspect of the disclosure.

According to a third aspect of the disclosure, there is provided a stretchable electronic device comprising a component according to the second aspect of the disclosure, and further comprising one or more electronic components soldered onto the layer of a conductive metal.

Advantageously, such a component has reliable interfacial adhesion between the stretchable silicone substrate and the one or more electronic components. Furthermore, such a component has an improved tensile strength in contact adhesion between the stretchable silicone substrate and the one or more electronic components.

Advantageously, soldering one or more electronic components to the conductive metal layer provides for the formation of irreversible bonding by metal alloying between the one or more electronic components and the conductive metal layer. Furthermore, advantageously, using soldering in the manufacturing process is minimally disruptive to large scale production.

Optionally, the one or more electronic components comprises one or more wires, integrated circuits, resistors, capacitors, microcontrollers, and/or other solid-state electronic components.

Optionally, the one or more electronic components are soldered to the conductive metal layer using tin solder. Optionally, the tin solder comprises tin-silver-copper (SAC), tin-silver, tin-copper, tin-silver-antimony, tin-antimony and/or tin-bismuth solder, and/or any other low temperature solder.

Optionally, the component according to the second aspect of the disclosure and/or the stretchable electronic device according to the third aspect of the disclosure may be configured to be mounted in or on and/or integrally formed with skin-mountable electronics, smart clothing, body conformable devices, or smart gloves.

According to a fourth aspect of the disclosure, there is provided a device for measuring chest expansion and deformation rate, comprising a stretchable electronic device according to the third aspect of the disclosure, and a silicone chest strap, wherein at least a portion of the second surface of the stretchable silicone substrate is attached to or integrally formed with the silicone chest strap.

Advantageously, such a device may provide for easier determination of breathing frequency. In particular, the device may be used to measure a number of peaks, corresponding to an inhalation and exhalation cycle, making it easier to determine breathing frequency. Furthermore, such a device may advantageously provide for the remote collection of data from active subjects/users during daily exercise. Such data may be used for exercise tracking, high impact sports tracking, diagnostics through looking at breathing patterns for patients with apnea, and/or rehabilitation for stroke patients.

Optionally, the silicone chest strap is configured to stretch when a user wearing the device inhales, and/or the silicone chest strap is configured to contract when the user exhales, such that the stretchable electronic device is configured to stretch when the user inhales and/or such that the stretchable electronic device is configured to contract or return to a relaxed state when the user exhales.

Optionally, the silicone chest strap comprises polydimethylsiloxane (PDMS).

According to a fifth aspect of the disclosure, there is provided a device for rehabilitation, comprising a stretchable electronic device according to the third aspect of the disclosure, and a silicone ball, wherein the stretchable electronic device is fully embedded in the silicone ball.

Advantageously, such a device may provide for the measurement of changes in resistance to reflect changes in pressure and the amount of pressure applied to the device by a user. For example, variations of squeeze-force with time could be used to monitor the rehabilitation of patients with hand injuries.

Optionally, the silicone ball is spherical and the stretchable electronic device is spherical or cubic.

Optionally, the stretchable electronic device is fully embedded in the silicone ball by co-curing.

Optionally, the silicone ball is configured to compress when a user squeezes or otherwise exerts a force on the silicone ball, and/or the silicone ball is configured to contract or return to a relaxed state when the user stops squeezing the silicone ball or reduces the amount of force exerted on the silicone ball, such that the stretchable electronic device is configured to compress and/or contract when the user squeezes or otherwise exerts a force on the silicone ball, and/or such that the stretchable electronic device is configured to expand and/or stretch and/or return to a relaxed state when the user stops squeezing the silicone ball or reduces the amount of force exerted on the silicone ball.

Optionally, the silicone ball comprises polydimethylsiloxane (PDMS).

According to a sixth aspect of the disclosure, there is provided a device for rehabilitation, comprising a stretchable electronic device according to the third aspect of the disclosure, and a silicone strap, wherein at least a portion of the stretchable silicone substrate is attached to or integrally formed with the silicone strap.

Advantageously, such a device may be useful in patient rehabilitation. In particular, such a device may be used to measure a number of peaks, corresponding to a tensile force applied to the silicone strap.

Optionally, the stretchable electronic device is configured to stretch when a tensile force is applied to the silicone strap, and/or the stretchable electronic device is configured to contract or return to a relaxed state when the tensile force is removed and/or decreased in magnitude.

Optionally, the silicone strap comprises a first portion and a second portion, wherein the first portion of the silicone strap comprises a loop for receiving a foot, ankle, leg, hand, wrist, arm, or other body part of a user, and wherein at least a portion of the stretchable silicone substrate is attached to or integrally formed with the second portion of the silicone strap.

Optionally, the silicone strap comprises polydimethylsiloxane (PDMS).

According to a seventh aspect of the disclosure, there is provided a device for sweat analysis, comprising a stretchable electronic device according to the third aspect of the disclosure, and a silicone strap, wherein at least a portion of the second surface of the stretchable silicone substrate is attached to or integrally formed with the silicone strap.

Optionally, the silicone strap may be configured to be worn as an armband around an arm.

Optionally, the stretchable electronic device may be configured to detect biological molecules in sweat.

Advantageously, such a device may be used as an electrode and may provide for easier sweat analysis of a subject/user. Furthermore, such a device may advantageously provide for the remote collection of data from active subjects/users during daily exercise. Such data may be used for exercise tracking, high impact sports tracking, and/or diagnostics through sweat analysis.

According to an eighth aspect of the disclosure, there is provided a device for sensing atmospheric NO2 or one or more other gases, comprising a stretchable electronic device according to the third aspect of the disclosure.

Optionally, the device may further comprise a silicone strap, wherein the silicone strap is configured to be worn by a user, for example, on or around an arm.

Advantageously, such a device may provide for easier sensing of atmospheric NO2 and/or other gases while a user is running.

According to a ninth aspect of the disclosure, there is provided a device for sensing exhaled breath gas of a user, comprising a stretchable electronic device according to the third aspect of the disclosure.

Advantageously, such a device may provide for easier detecting of nitrogenous gases in exhaled breath gas. Such data may be useful in diagnostics.

BRIEF DESCRIPTION OF THE DRAWINGS

The present disclosure may be carried out in various ways and embodiments of the disclosure will now be described by way of example with reference to the accompanying drawings, in which.

DETAILED DESCRIPTION

Figure 1:
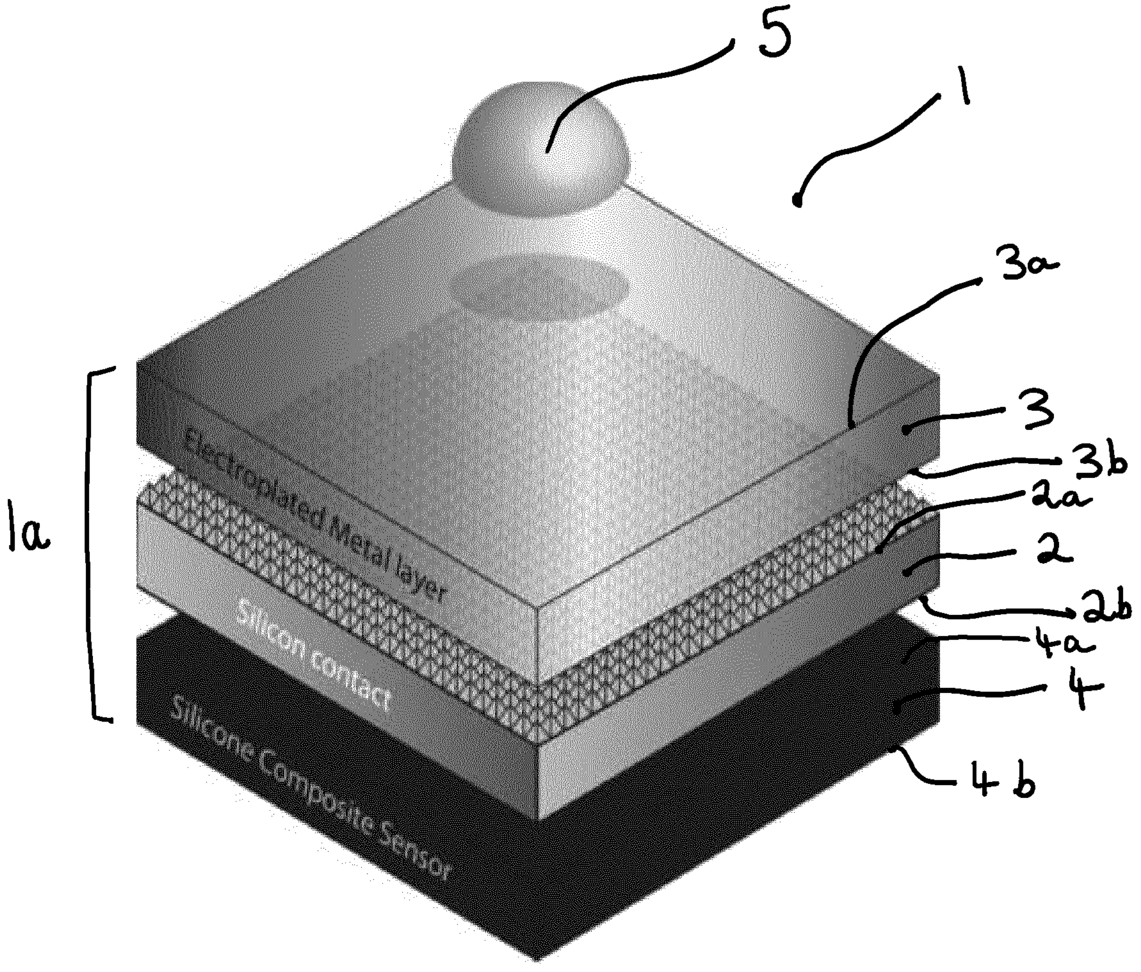
FIG. 1 shows a schematic exploded view of a stretchable electronic device.

FIG. 1 shows a schematic exploded view of a stretchable electronic device 1. The stretchable electronic device 1 comprises a component 1*a* and one or more electronic components 5. The component 1*a* includes a silicon wafer 2, a layer of a conductive metal 3 and a stretchable silicone substrate 4.

The silicon wafer 2 has a first surface 2*a* and a second surface 2*b*. In the example shown in FIG. 1, the silicon wafer 2 is quadrilateral. Though, it is envisaged that the silicon wafer 2 may have any other shape. For example, the silicon wafer 2 may be circular. The silicon wafer 2 has a thickness of approximately 525 μm.

The layer of a conductive metal 3 has a first surface 3*a* and a second surface 3*b*. The layer of a conductive metal 3 is arranged adjacent to the silicon wafer 2. In particular, the second surface 3*b* of the layer of a conductive metal 3 is arranged adjacent the first surface 2*a* of the silicon wafer 2. More particularly, the layer of a conductive metal 3 (specifically the second surface 3*b* thereof) is applied onto at least a portion of the first surface 2*a* of the silicon wafer 2. In the example shown in FIG. 1, the layer of a conductive metal 3 is quadrilateral. Though, it is envisaged that the layer of a conductive metal 3 may have any other shape. The layer of a conductive metal 3 has a thickness of approximately 1 μm.

The stretchable silicone substrate 4 has a first surface 4*a* and a second surface 4*b*. The stretchable silicone substrate 4 is arranged adjacent to the silicon wafer 2. In particular, the first surface 4*a* of the stretchable silicone substrate 4 is arranged adjacent the second surface 2*b* of the silicon wafer 2. More particularly, the stretchable silicone substrate 4 (specifically at least a portion of the first surface 4*a* thereof) is plasma bonded to the silicon wafer 2 (specifically to at least a portion of the second surface 2*b* thereof). In the example shown in FIG. 1, the stretchable silicone substrate 4 is quadrilateral. Though, it is envisaged that the stretchable silicone substrate 4 may have any other shape. For example, the stretchable silicone substrate 4 may have any two-dimensional shape such as a circle, or any three-dimensional shape such as a cuboid or sphere.

The one or more electronic components 5 are arranged adjacent the layer of a conductive metal 3. In particular, the one or more electronic components 5 are arranged adjacent the first surface 3*a* of the layer of a conductive metal 3.

The silicon wafer 2 comprises crystalline silicon and is a lightly doped p-type silicon wafer.

The layer of a conductive metal 3 comprises copper. Though, it is envisaged that the layer of a conductive metal 3 may comprise any suitable metal. For example, the layer of a conductive metal 3 may comprise, for example, one or more of copper, gold, nickel, cadmium, rhodium, platinum, silver and zinc.

Figures 4A, 4B, 4C:
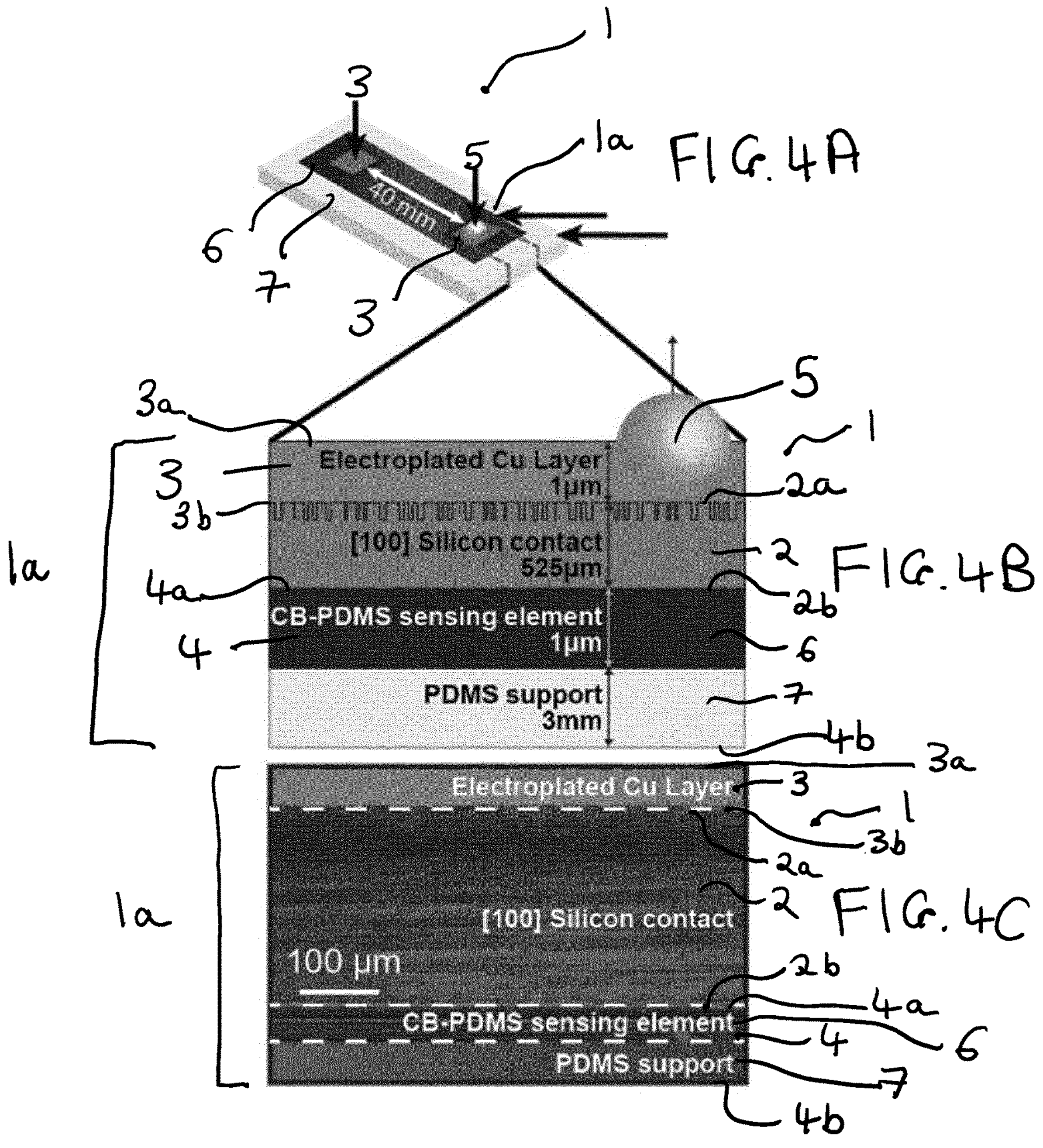
FIG. 4A shows a schematic isometric view of a stretchable electronic device.
FIG. 4B shows a schematic cross-sectional view of the stretchable electronic device shown in FIG. 4A.
FIG. 4C shows a cross-sectional optical monography image of a component of the stretchable electronic device shown in FIGS. 4A and 4B.

The stretchable silicone substrate 4 comprises a first layer 6 and a second layer 7. The first layer 6 of the stretchable silicone substrate 4 comprises the first surface 4*a* of the stretchable silicone substrate 4, and the second layer 7 of the stretchable silicone substrate 4 comprises the second surface 4*b* of the stretchable silicone substrate 4. This is shown in the schematic cross-sectional view of FIG. 4B, and also in the schematic isometric view of FIG. 4A, which both show a stretchable electronic device 1 similar to the stretchable electronic device 1 shown in FIG. 1. Although FIG. 4B shows a cross-sectional view of the stretchable electronic device 1 shown in FIG. 4A, the cross-sectional view of FIG. 4B also demonstrates a cross-section of the stretchable electronic device 1 shown in FIG. 1. The first layer 6 of the stretchable silicone substrate 4 has a thickness of approximately 1 μm. The second layer 7 of the stretchable silicone substrate 4 has a thickness of approximately 3 mm.

The first layer 6 of the stretchable silicone substrate 4 comprises carbon black-filled polydimethylsiloxane (CB-PDMS), and the second layer 7 of the stretchable silicone substrate 4 comprises polydimethylsiloxane (PDMS). Though, it is envisaged that the first layer 6 of the stretchable silicone substrate 4 may comprise any other silicone material comprising a plurality of conductive particle fillers and/or one or more conductive liquids dispersed in a silicone polymer matrix, and/or that the second layer 7 of the stretchable silicone substrate 4 may comprise any other suitable silicone material. The concentration of carbon black, or other conductive particle fillers or conductive liquids in the first layer 6 of the stretchable silicone substrate 4 may be chosen, during the process of designing the stretchable silicone substrate 4, to optimise the resistance and binding strength of the stretchable silicone substrate 4. The optimum concentration of carbon black in the CB-PDMS first layer 6 of the stretchable silicone substrate 4 has been found to be between 5-20%, preferably 12%. Advantageously, such a carbon black concentration can provide an optimum electrical resistance in the first layer 6 of the stretchable silicone substrate 4. Furthermore, such a carbon black concentration may balance the effects of conductivity increasing with carbon black content, with the agglomeration of carbon black particles on the surface of the first layer 6 of the stretchable silicone substrate 4. Advantageously, balancing these effects prevents a reduction in the adhesive interaction of polydimethylsiloxane (PDMS) with carbon black (CB). In addition, such a carbon black concentration may provide a low electrical resistance in the first layer 6 of the stretchable silicone substrate 4, when the component 1*a* is configured to operate with a 3.3V and/or 5V circuit, and may also provide high binding strength.

Advantageously, polydimethylsiloxane (PDMS) provides for reduced cost and ease of manufacture of the component 1*a*. Advantageously, having carbon black or other conductive particle fillers or conductive liquids in the first layer 6 of the stretchable silicone substrate 4 provides the stretchable silicone substrate with improved long-term chemical and mechanical stability, and a low cost. Furthermore, having carbon black or other conductive particle fillers or conductive liquids in the first layer 6 of the stretchable silicone substrate 4 may also provide the component 1*a* with tunable mechanical and/or electrical properties.

The one or more electronic components 5 comprises one or more wires, integrated circuits, resistors, capacitors, microcontrollers, and/or other solid-state electronic components. In FIGS. 1, 4A and 4B, just one exemplary schematic electronic component 5 is shown, for the sake of simplicity and clarity.

Figure 2:
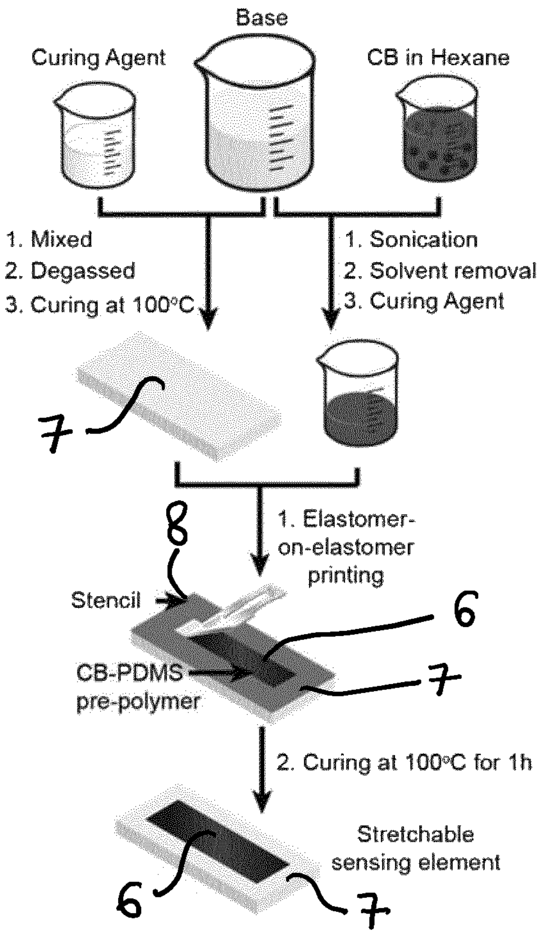
FIG. 2 shows a schematic representation of a method of fabricating a stretchable silicone substrate.

With reference firstly to FIG. 2, an exemplary method of manufacturing a component 1*a* and stretchable electronic device 1 as shown in FIGS. 1, 4A and 4B shall now be described.

To obtain the PDMS second layer 7 of the stretchable silicone substrate 4, a curing agent and a base elastomer are mixed, degassed, and cured at 100 degrees centigrade.

To obtain the CB-PDMS first layer 6 of the stretchable silicone substrate 4, sonication, solvent removal, and a curing agent are applied to a base elastomer and a suspension of powdered carbon black, 50 nm particle size, in hexane.

Next, by a process of elastomer-on-elastomer printing, the CB-PDMS first layer 6 is printed on top of the PDMS second layer 7. A stencil mask 8 is applied onto the PDMS second layer 7 such that the CB-PDMS first layer 6 covers only a portion of the surface of the PDMS second layer 7. The stencil mask 8 is cut using a CO2-beam cutter. Once the CB-PDMS first layer 6 has been printed onto the PDMS second layer 7, the first layer 6 and the second layer 7 are cured in an oven for one hour, at a temperature of 100 degrees centigrade. Though, it is envisaged that a curing time of less than one hour and/or a temperature of less than or equal to 150 degrees centigrade may also be used. Advantageously, a curing time of less than one hour may provide for reduced particle transfer of the plurality of conductive particle fillers and/or one or more conductive liquids from the first layer 6 of the stretchable silicone substrate 4 to the second layer 7 of the stretchable silicone substrate 4, which would otherwise disrupt the percolation network and lower the conductivity of the first layer 6 of the stretchable silicone substrate 4. Advantageously, a curing temperature of less than 150 degrees centigrade enables the plurality of conductive particle fillers and/or one or more conductive liquids in the first layer 6 of the stretchable silicone substrate 4 to establish good contact prior to gelation. It is also envisaged that if the temperature is less than 150 degrees centigrade, a curing time of up to 48 hours may be used.

In the example shown in FIG. 2, the first layer 6 and the second layer 7 are shown as being quadrilateral, for the sake of simplicity and clarity. Though, it is envisaged that the first layer 6 and/or the second layer 7 may be any other shape, as the above described process is applicable to more complex shapes.

In order to apply the layer of a conductive metal 3, which in the examples described above and shown in FIGS. 1, 3C and 4 comprises copper, firstly, the first surface 2*a* of the silicon wafer 2 is plated electrolessly with silver and the second surface 2*b* of the silicon wafer 2 is covered with a polyimide film/sheet. Plating silver onto the first surface 2*a* of the silicon wafer 2 serves to assist the etching process, and covering the second surface 2*b* of the silicon wafer 2 protects said surface to preserve an atomically flat surface ideal for conformal plasma bonding later with the stretchable silicone substrate 4. The layer of polyimide is later removed from the second surface 2*b* of the silicon wafer 2. Next, the first surface 2*a* of the silicon wafer 2 is placed in an etching solution containing $H_2O_2$ and hydrogen fluoride in order to provide the first surface 2*a* with a nanoporous surface. In other words, the first surface 2*a* of the silicon wafer 2 is etched so that it is roughened and becomes nanoporous. Metal-assisted chemical etching is used. The second surface 2*b* of the silicon wafer 2 is not etched and is smooth compared with the first surface 2*a* of the silicon wafer 2. Then, the layer of a conductive metal 3, which comprises copper, is deposited on top of the roughened, nanoporous first surface 2*a* of the silicon wafer 2 using electroplating. The copper electroplating is performed in a 0.8 M $CuSO_4$ aqueous solution with a few drops of ethanol, using a platinum wire as the anode an applying a current density of 0.20 $mAcm^{-1}$ for 15 minutes.

Advantageously, etching at least a portion of the first surface 2*a* of the silicon wafer 2 provides for increased surface contact adhesion between the silicon wafer 2 and the layer of a conductive metal 3. This advantageously enables soldering to take place on the component 1*a*. Furthermore, etching at least a portion of the first surface 2*a* of the silicon wafer 2 may also provide for a reduction or even a complete elimination of the need to have an interfacial layer between the silicon wafer 2 and the layer of a conductive metal 3.

Figure 3A:
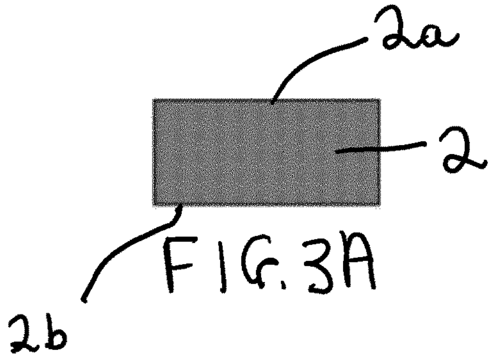
FIG. 3A shows a schematic cross-sectional view of a pristine silicon wafer.
Figure 3B:
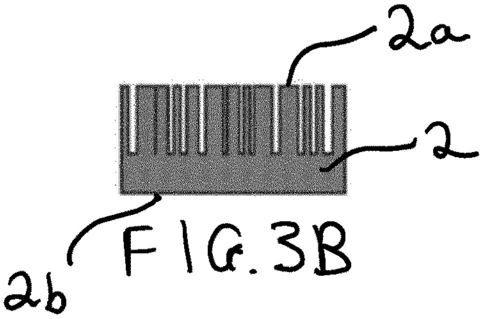
FIG. 3B shows a schematic cross-sectional view of the silicon wafer shown in FIG. 3A, after it has been etched using metal-assisted chemical etching.
Figure 3C:
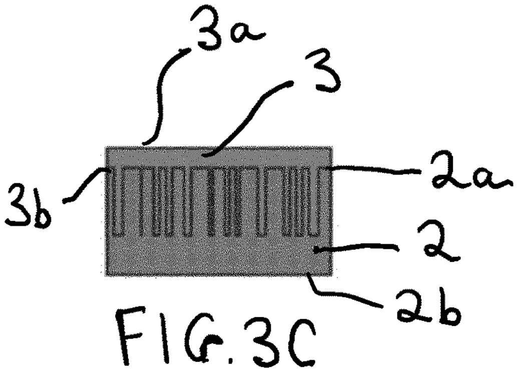
FIG. 3C shows a schematic cross-sectional view of the etched silicon wafer shown in FIG. 3B, after it has had a layer of copper electroplated on top of it.
Figure 3D:
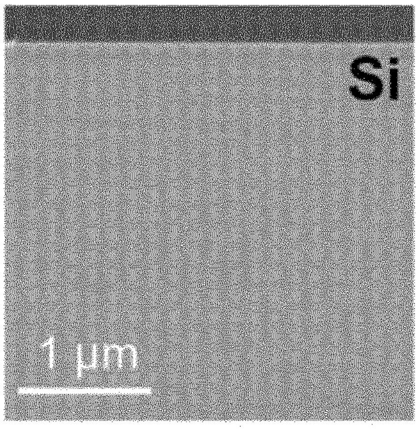
FIG. 3D shows a cross-sectional SEM image of the silicon wafer shown in FIG. 3A
Figure 3E:
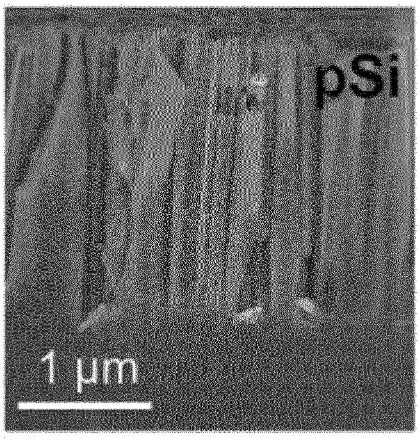
FIG. 3E shows a cross-sectional SEM image of the etched silicon wafer shown in FIG. 3B.
Figure 3F:
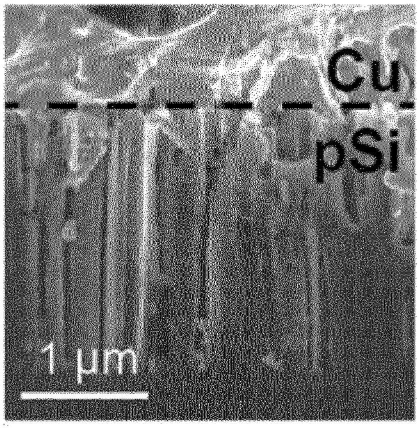
FIG. 3F shows a cross-sectional SEM image of the etched silicon wafer and the layer of copper as shown in FIG. 3C.

FIG. 3A shows the silicon wafer 2 before the first surface 2*a* of the silicon wafer 2 is etched. FIG. 3B shows the silicon wafer 2 after the first surface 2*a* of the silicon wafer 2 has been etched. FIG. 3C shows the layer of a conductive metal 3 electroplated on the roughened first surface 2*a* of the silicon wafer 2. FIGS. 3D-F show cross-sectional SEM images taken of the silicon wafer 2 and the layer of a conductive metal 3 as schematically shown in cross-section in FIGS. 3A-C respectively.

In order to bond the second surface 2*b* of the silicon wafer 2 to the first surface 4*a* of the stretchable silicone substrate 4, plasma bonding is used. Firstly, after being cleaned using acetone, the stretchable silicone substrate 4 and the second surface 2*b* of the silicon wafer 2 are treated in 100% O2 plasma for an operating time of 35 seconds, using, for example, a Gala Instrumente Plasma Prep 5 Cleaner. Advantageously, treating said surfaces in 100% O2 plasma activates said surfaces by generation of a silicon oxide layer. Next, the silicon wafer 2 is arranged/held adjacent the stretchable silicone substrate 4 with a gap of approximately 40 mm therebetween, while the one or more electronic components 5 are soldered onto the layer of a conductive metal 3 (specifically, onto the first surface 3*a* of the layer of a conductive metal 3) using tin solder. Advantageously, this provides for the formation of irreversible bonding by metal alloying between the one of more electronic components 5 and the layer of a conductive metal 3. The component 1*a* has reliable interfacial adhesion between the stretchable silicone substrate 4 and the one or more electronic components 5, and has an improved tensile strength in contact adhesion between the stretchable silicone substrate 4 and the one or more electronic components 5. Furthermore, using soldering in the manufacturing process is minimally disruptive to large scale production. Next, the second surface 2*b* of the silicon wafer 2 is bonded to the first surface 4*a* of the stretchable silicone substrate 4 by providing conformal contact between the second surface 2b of the silicon wafer 2 and the first surface 4a of the stretchable silicone substrate 4. Then, light pressure is applied (for example, simply by pressing the silicon wafer 2 and the stretchable silicone substrate 4 together using one's hands) to the silicon wafer 2 and the stretchable silicone substrate 4 for approximately 30 seconds. Care should be taken to not press down on the one or more electronic components 5 too much, as deformation of the elastic, activated stretchable silicone substrate 4 may break some of the newly-formed bonds. Next, the assembly is left to stabilise at room temperature for approximately 3 days.

In the example shown in FIG. 1, the silicon wafer 2 is configured to cover the entire surface of the stretchable silicone substrate 4. However, as shown in FIG. 4A for example, it is also envisaged that only a portion of the second surface 2b of the silicon wafer 2 may be bonded to only a portion of the first surface 4a of the stretchable silicone substrate 4. In other words, the silicon wafer 2 does not need to cover the entirety of the first surface 4a of the stretchable silicone substrate 4. Accordingly, a mask (not shown), which may for example be made out of a polymer film, can be used to expose only one or more predetermined areas of the first surface 4a of the stretchable silicone substrate 4 to the plasma treatment/plasma bonding process. Siloxane cross-linking occurs on the surface of polydimethylsiloxane (PDMS) after plasma treatment, which makes the surface locally more brittle, so using a mask can help preserve the mechanical properties of the stretchable silicone substrate 4.

Plasma bonding the silicon wafer 2 to the stretchable silicone substrate 4 provides covalent bonding between the silicon wafer 2 and the stretchable silicone substrate 4, specifically between at least a portion of the second surface 2b of the silicon wafer 2 and at least a portion of the first surface 4a of the stretchable silicone substrate 4b. The cross-sectional view of FIG. 4B illustrates the covalent bonding between the silicon wafer 2 and the stretchable silicone substrate 4 and the penetration of copper in the layer of a conductive metal 3 with the roughened first surface 2a of the silicon wafer 2.

Advantageously, the component 1a provides a means to bond silicones to stretchable electronics, and the component 1a has significantly reduced complexity, reduced manufacturing time, lower operational costs, improved miniaturisation, improved versatility, improved applicability, improved imperceptibility, reduced weight, and reduced manufacturing cost. In addition, the component 1a provides improved adhesion force between hard and soft electronics in a strain sensing system. In particular, the component 1a has increased mechanical strength, durability and reliability. More particularly, the component 1a can withstand large stresses and/or strains and is thus suitable for use in a wearable device, where reliability under fast strain rates and tensile forces is essential, for example where forces larger than 2 MPa may typically be exerted.

Advantageously, the component 1a also provides reliable interfacial adhesion between soft stretchable electronic elements (such as the stretchable silicone substrate) and conventional inelastic hard electronics. Plasma bonding the silicon wafer 2 to the stretchable silicone substrate 4 exploits the chemistry of silicon and silicone and provides a reliable interface by covalent bonding.

Furthermore, the fabrication process for manufacturing the component 1a is simple, in that the component can be manufactured in a standard laboratory environment, i.e. without the need for advanced facilities such as a clean room. The component 1a is therefore suitable for large scale manufacturing under normal conditions.

Additionally, the component 1a and the stretchable electronic device 1 provide for creating solderable, mechanically robust, electrical contacts to interface silicone-based strain sensors with conventional solid-state (hard) electronics.

Plasma bonding at least a portion of the second surface 2b of the silicon wafer 2 to at least a portion of the first surface 4a of the stretchable silicone substrate 4 provides for covalent and conformal adhesion between the silicon wafer 2 and the stretchable silicone substrate 4. Advantageously, this provides for a strong and reliable bond between the silicon wafer 2 and the stretchable silicone substrate 4. In addition, advantageously, the stretchable silicone substrate 4 remains stretchable even after being bonded to the silicon wafer 2.

In addition, the component 1a has improved elasticity.

Furthermore, the component 1a has improved interfacial adhesion such that the component 1a may fail in an abrupt manner rather than in a gradual manner. For example, when the component 1a is used in a stretchable electronic device 1 configured to measure a signal, if one or more of the interface between the layer of a conductive metal 3 and the silicon wafer 2 or the interface between the silicon wafer 2 and the stretchable silicone substrate 4 fails, the loss of signal from the stretchable electronic device 1 is abrupt rather than gradually decreasing. This is advantageous so that a user may be able to readily realise with increased certainty and/or obviousness when a stretchable electronic device 1 has failed. Such performance shall be discussed below in more detail.

Additionally, the component 1a provides for the monolithic integration of electronic components 5 and data-transmission elements with a stretchable electronic device 1, which enables improves reliability, miniaturisation and simplification of a stretchable electronic device 1. Furthermore, the integration of such electronic components 5 with the stretchable silicone substrate 4 may provide for decreased size, decreased weight and improved mass production of a component 1a for a stretchable electronic device 1. Such a component 1a can also provide for a comfortable and imperceptible wearable sensor, user-friendly remote tracking, and personal healthcare control.

The present inventors have compared the mechanical properties and electrical performance of the component 1a with prior art devices using AgEpoxy adhesive, as shall be described below with reference to FIGS. 5A to 7C.

Figure 5A:
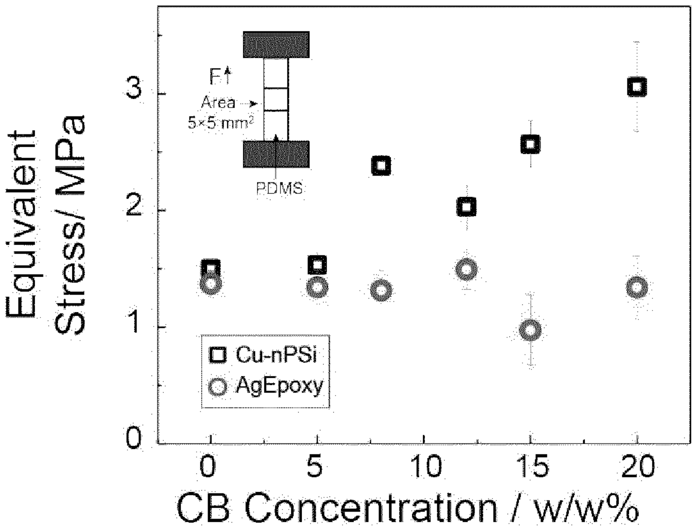
FIG. 5A shows the dependence of break stress and strain of a component compared with a prior art component, for varying carbon black filler concentrations.

FIG. 5A shows the dependence of break stress and strain of the component 1a (labelled "Cu-nPSi" in FIGS. 5A-C) compared with a prior art component, for varying carbon black concentrations. The prior art component comprises silver-based conductive epoxy (AgEpoxy, labelled "AgEpoxy" in FIGS. 5A-C) contacts on CB-PDMS. The data shown in FIGS. 5A-C thus compares the performance of Cu-nPSi contacts on CB-PDMS (as in the component 1a) with the performance of AgEpoxy contacts on CB-PDMS. Samples having concentrations of between 5 and 20% of carbon black in CB-PDMS were made and tested. FIG. 2A shows that with increasing concentration of carbon black in CB-PDMS, higher stress is required to separate adhesive entities as the modulus of the bulk material increases. At the same time, as the carbon black content increases along with the conductivity of the CB-PDMS, particles agglomerate on the surface of the composite which could reduce the adhesive interaction of carbon black with PDMS in CB-PDMS. However, this effect is not observed in the range of 5-20% carbon black. The granular nature of AgEpoxy can be a source of non-uniform coverage of epoxy on the adhesion interface with CB-PDMS, and air pockets which could serve as areas of high stress could lead to crack formation in multiple sites, thus causing lower overall breaking stress for samples at all concentrations of carbon black, as well as progressive cracking and loss of electrical signal at higher stress levels. The comparatively poor performance of AgEpoxy contacts on CB-PDMS compared with the improved performance of Cu-nPSi contacts on CB-PDMS is shown in clearly shown in FIG. 5A.

Figure 5B:
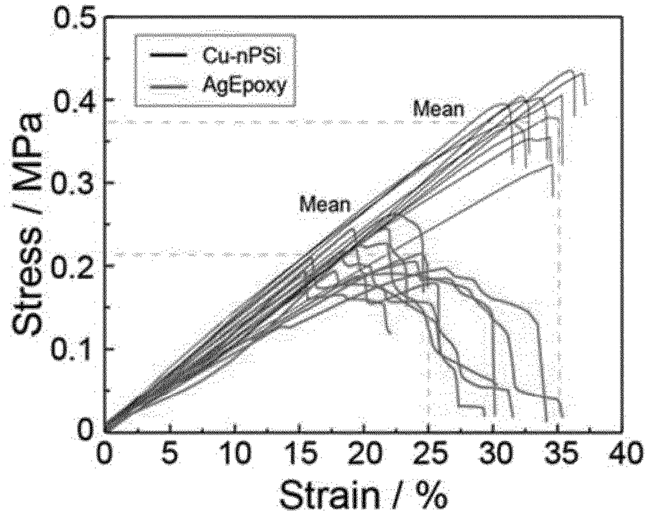
FIG. 5B shows the ultimate stress and strain at fail during a single stretch from rest for polydimethylsiloxane (PDMS) samples with different contacts.
Figure 5C:
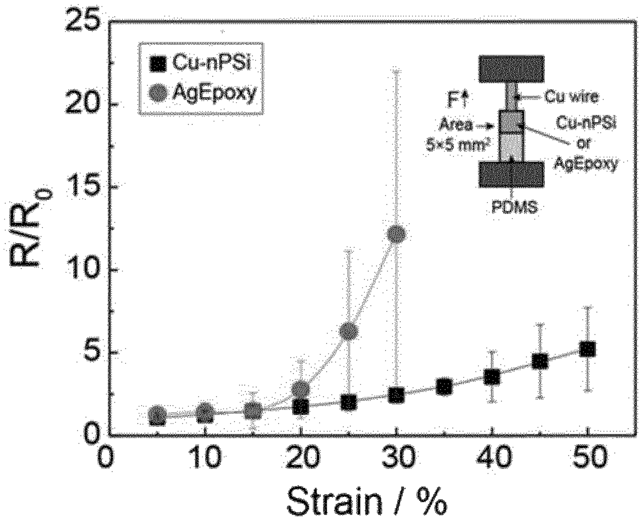
FIG. 5C shows the piezoresistive behaviour of carbon black-filled polydimethylsiloxane (PDMS) sample with different contacts.

To investigate the electromechanical behaviour of the samples described above in relation to FIG. 5A, strain and maximum stress tests were performed on samples stretched by copper wires attached to the contacts. The results are shown in FIG. 5B. FIG. 5B shows the mode of failure for devices made using Cu-nPSi contacts on CB-PDMS (as in the component 1*a*) and AgEpoxy contacts on CB-PDMS. Imperfections and crack prone voids caused the breaking of several AgEpoxy samples in a stepwise fashion starting at 0.20 MPa and 20% strain. The Cu-nPSi contacts were found to fail catastrophically at 35% strain on average and at 0.42 MPa. The failure shown in the Cu-nPSi is more desirable. This is because as shown in FIG. 5C, the gradual failure mode of failure of the AgEpoxy contacts creates large discrepancies in the electrical signal measured as resistance change with strain of the CB-PDMS composite, producing large errors in the typical exponential signal. The catastrophic failure of the CU-nPsi is more desirable because it provides that a component 1*a* may fail abruptly rather than gradually. A loss in signal may therefore be sudden, so that a user of the component 1*a* may advantageously be able to readily realise with increased certainty and/or obviousness when the component 1*a* has failed.

Figure 6A:
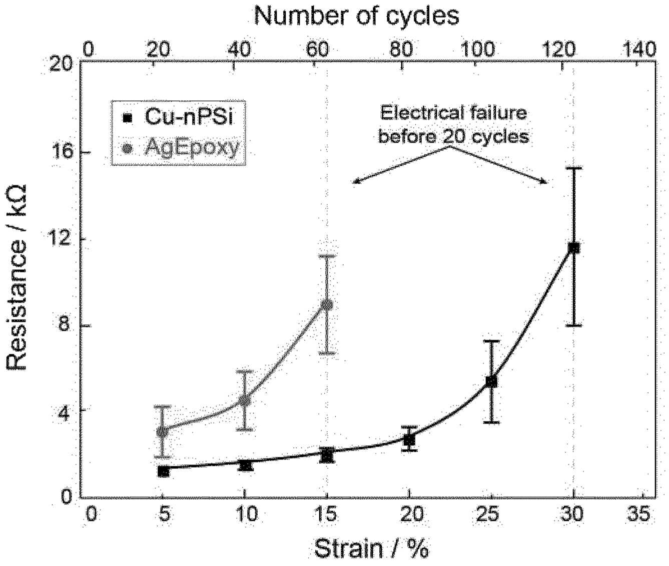
FIG. 6A shows the resistance after 20 cycles of strain and release at different strain levels of a component compared with a prior art component.

FIG. 6A shows a comparison of the resistance after 20 cycles of strain and release at different strain levels for Cu-nPSi contacts on CB-PDMS (as in the component 1*a*) with the performance of AgEpoxy contacts on CB-PDMS (similar samples to those described above in relation to FIG. 5 were used). The cyclic deformation of the contacts was studied by measuring the resistance and mechanical properties at a constant strain and with an increase of 5% elongation every 20 cycles at 2.5 mm/s. FIG. 6A shows the resistance measured at the end of each stage. Lower maximum strains were observed for both contacts, with the AgEpoxy contacts breaking at around 20% strain ($\sigma$=0.20 MPa) and the Cu-nPSi contacts breaking at around 30% strain ($\sigma$=0.38 MPa). The exponential shape of the response can be attributed to a well characterised hysteresis effect coming from the PDMS matrix at higher strains, whereas a more rapid restoration of conductivity occurs at strains below 15%. The large increase in the case of the AgEpoxy contacts can also be due to the brittleness of the contacts as cracks would cause large area disconnections at large values of strain.

Figure 6B:
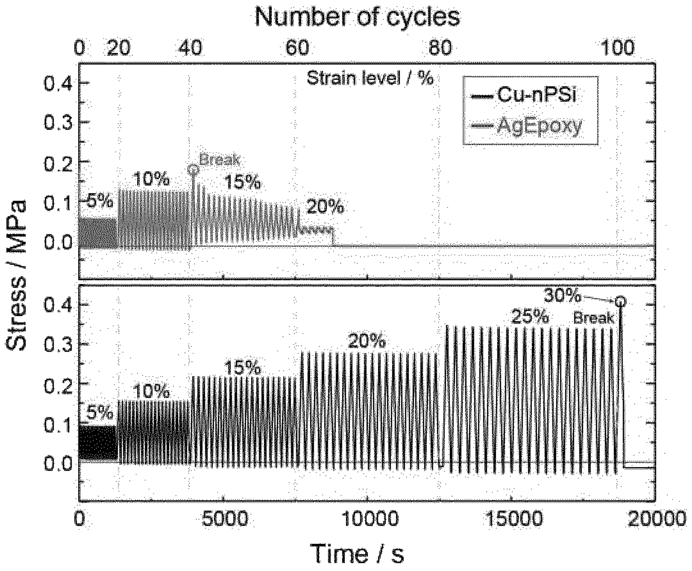
FIG. 6B shows a demonstration of the break mechanism of a component compared with a prior art component.

Sensor performance also depends on the failure of the component bond at a certain strain level and after cyclic strain. A gradual break rather than a sudden break would result in loss of electrical signal and therefore loss of functionality of the component. The conductive properties of the AgEpoxy contacts on CB-PDMS were found to diminish with increasing strains much faster than the conductive properties of the Cu-nPSi contacts on CB-PDMS. As illustrated in FIG. 6B, the adhesive interaction between AgEpoxy and CB-PDMS was shown to be weaker and crack at strains of 15% reaching strains of up to 20%, whereas the Cu-nPSi contacts were shown to be reliable after 100 incremental cycles up to 25% strain and to be able to withstand strains of up to 35%.

FIGS. 5B, 5C, 6A and 6B illustrate that AgEpoxy contacts gradually fail, resulting in a gradual decrease in signal for a component, whereas desirably, Cu-nPSi contacts fail with an abrupt loss of signal and fail at a higher strain level.

Figure 7A:
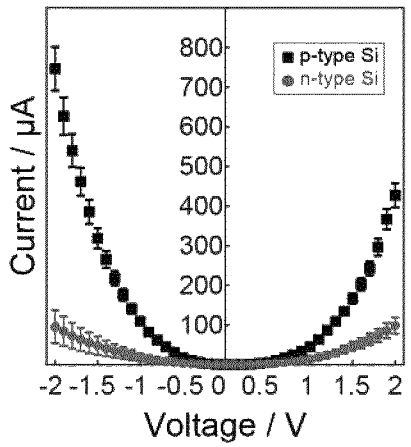
FIG. 7A shows current-voltage curves for components using lightly doped p-type and n-type silicon.
Figure 7B:
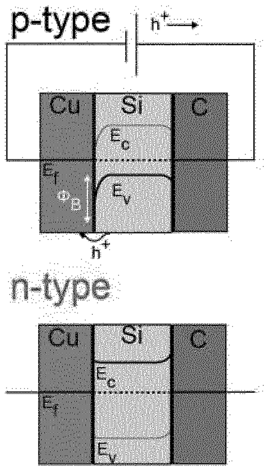
FIG. 7B shows a Schottky junction band diagram for a component having a p-type silicon contact and for a component having an n-type silicon contact.

To study the effect of the Schottky diode formed at the interface of the component 1*a*, two types of Cu-nPSi contacts on CB-PDMS with different conduction mechanisms, namely p-type and n-type semiconductors, were tested. FIG. 7A shows current-voltage curves for components 1*a* having p-type and n-type silicon. FIG. 7A shows that for p-type silicon, currents of lower magnitude can be obtained with positive applied voltages compared with n-type silicon. This is observed in the non-linear regime of the current-voltage (I-V) curves, applying a voltage from −1.0V to +1.0V. An applied voltage with magnitude higher than 1.0V is therefore required for strain-sensing with the component 1*a*. The component 1*a* contact structure leads to Schottky junctions at both silicon heterointerfaces, for both p-type and n-type silicon. Fermi level pinning causes bending in the silicon conduction and valence bands. This is shown in FIG. 7B, and restricts the conductance at low energies.

Figure 7C:
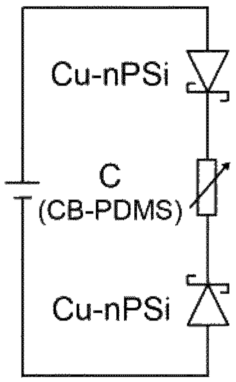
FIG. 7C shows an equivalent circuit representing the assemblies shown in FIG. 7B as Schottky junctions in appropriate directions.

The resistance of p-type silicon is known to be lower than that of n-type silicon, with resistance values of 175.5 kΩ and 68.3 kΩ, respectively. The greatest obtained component 1*a* contact conductance was (1.63±0.04)x10-5Ω-1, for p-type silicon applying a negative voltage. Asymmetry in the p-type curve is explained by the Schottky barrier height at the Cu—Si interface. The largest Schottky barrier height $\phi B$ is the Si—Cu interface (assuming a Cu work function of −4.65 eV 45), which must be overcome for hole transport. The p-type contacts are therefore more conductive in the direction shown in FIG. 7B, i.e. with hole (h+) transport from Si to Cu, because this avoids the largest potential barrier from the Cu Fermi level (Ef) over the Schottky barrier $\phi B$ to the Si valence band (Ev). Band bending for both n-type device architectures is also shown in FIG. 7B, where electron transport occurs in the silicon conduction band (Ec). Using silicon with higher doping levels would increase the charge carrier density and thereby reduce the width of the band bending. Using thin silicon layers (<100 μm) as contacts would effectively reduce the Schottky barrier height for charge transport from silicon into the metallic conductors, as each metal-Si Schottky barrier would sit within the band bending regime of the other. An equivalent circuit diagram is presented in FIG. 7C representing the circuit where the CB-PDMS piezoresistive element is connected via the solder-Cu-nPSi contacts to a power source to produce the I-V curves.

Figure 8A:
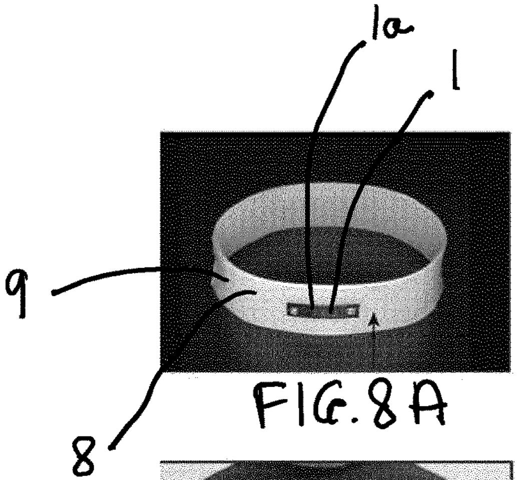
FIG. 8A shows a device for measuring expansion and deformation rate.
Figure 8B:
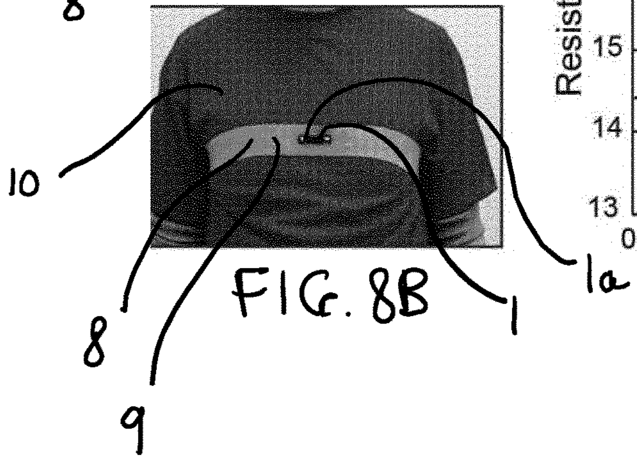
FIG. 8B shows a user wearing the device of FIG. 8A.
Figure 8C:
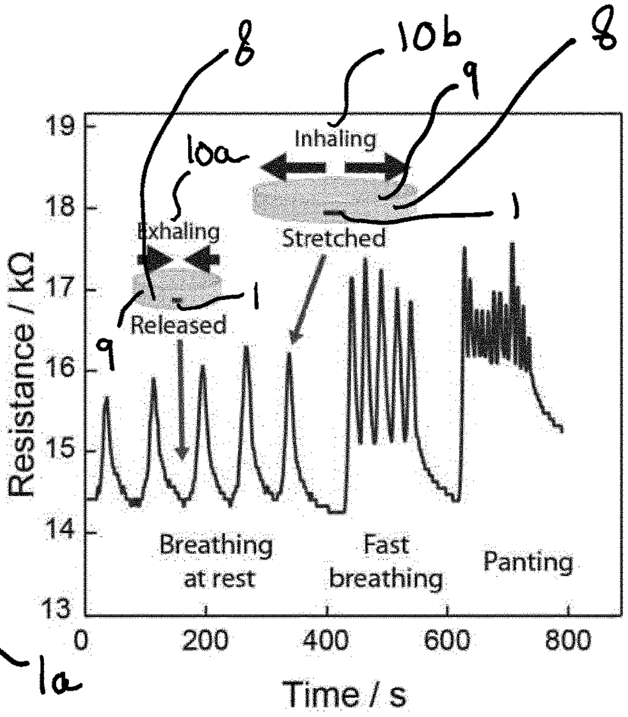
FIG. 8C shows physiological data collected from chest expansion during inhalation and exhalation of a user wearing the device of FIG. 8A, recorded as changes in resistance.

As shown in FIGS. 8A-C, the component 1*a* and the stretchable electronic device 1 may be part of a device 8 for measuring chest expansion and deformation rate. The device 8 comprises the stretchable electronic device 1 and a silicone chest strap 9. At least a portion of the silicone chest strap 9 is attached to or integrally formed with at least a portion of the stretchable silicone substrate 4. In the example shown in FIG. 8A, the second surface 4*b* of the stretchable silicone substrate 4 is printed on the silicone chest strap 9 such that it is integrally formed with the silicone chest strap 9. The silicone chest strap 9 comprises a strip of silicone having a first end and a second end joined together to form a closed loop, as shown in FIG. 8A, and is made from polydimethylsiloxane (PDMS). As shown in FIG. 8B, the silicone chest strap 9 is sized to be worn as a harness around the chest of a user 10. The width and/or looped length of the silicone chest strap 9 may be sized depending on, for example, one or more of the age, gender, and weight of the user 10.

When a user 10 wearing the device 8 inhales, the silicone chest strap 9 and the stretchable silicone substrate 4 are configured to stretch to a stretched position 10*b*, as shown in FIG. 8C. When a user 10 wearing the device 8 exhales, the silicone chest strap 9 and the stretchable silicone substrate 4 are configured to contract or return to a relaxed/released position 10*a*, as shown in FIG. 8C.

FIG. 8C shows the resistance change corresponding to the chest expansion of a user 10 at rest. Each of the peaks shown in FIG. 8C corresponds to an inhalation and exhalation cycle. This makes it easy to determine breathing frequency by tracking the resistance change while a user 10 is wearing the device 8. Using the device 8, it is possible to remotely collect date from active subjects during daily exercise and construct health and progress graphs, with an additional wireless antenna. Accordingly, the device 8 can be used for exercise tracking, high impact sports tracking, diagnostics through breathing for patients with apnea, and rehabilitation for stroke patients.

As shown in FIGS. 9A-F, the stretchable electronic device 1 may be part of a device 11 for rehabilitation. The device 11 comprises the stretchable electronic device 1 and a silicone ball 12. The stretchable electronic device 1 is fully embedded in the silicone ball 12, as shown in the cross-sectional view of FIG. 9C.

Figure 9A:
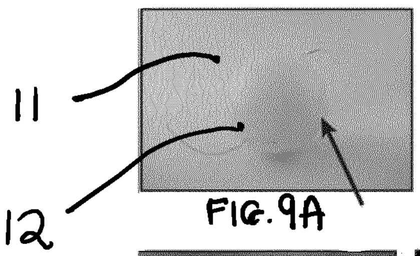
FIG. 9A shows a device for rehabilitation.
Figure 9B:
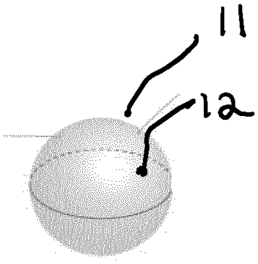
FIG. 9B shows a device for rehabilitation.
Figure 9C:
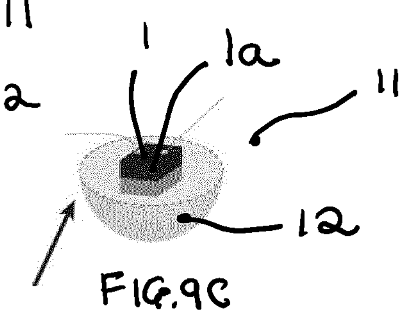
FIG. 9C shows a cross-sectional view of the device shown in FIG. 9B.
Figure 9D:
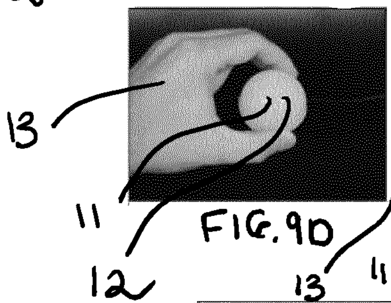
FIG. 9D shows a user holding the device of FIG. 9A.
Figure 9E:
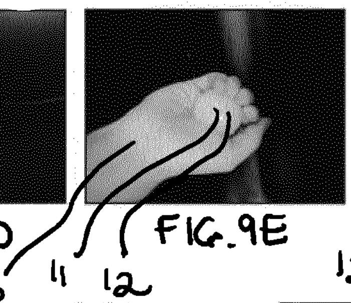
FIG. 9E shows a user softly gripping the device of FIG. 9A.
Figure 9F:
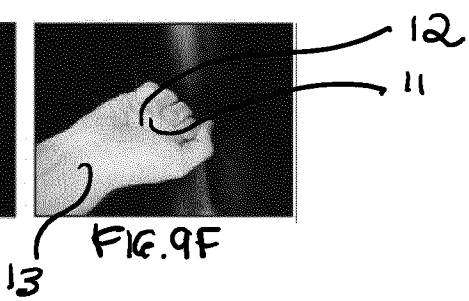
FIG. 9F shows a user tightly gripping the device of FIG. 9A.
Figure 9G:
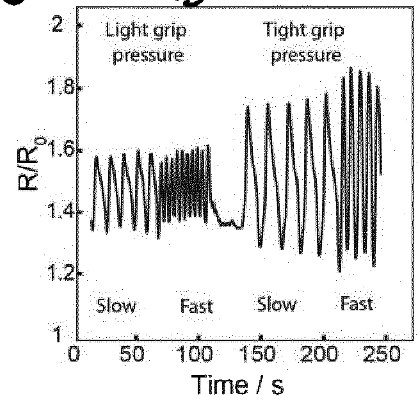
FIG. 9G shows resistance data collected using the device of FIG. 9A during exercise at light gripping pressure and tight gripping pressure at different exercise rates.
Figure 9H:
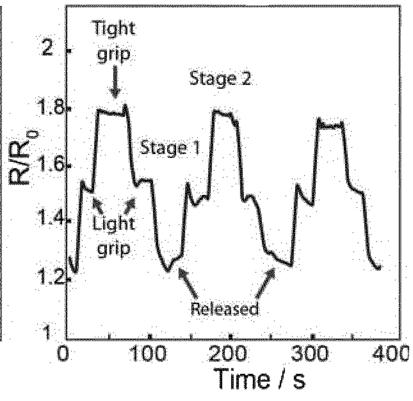
FIG. 9H shows resistance data collected using the device of FIG. 9A by applying different pressures and recording stepwise transitions of electrical signal.
Figure 9I:
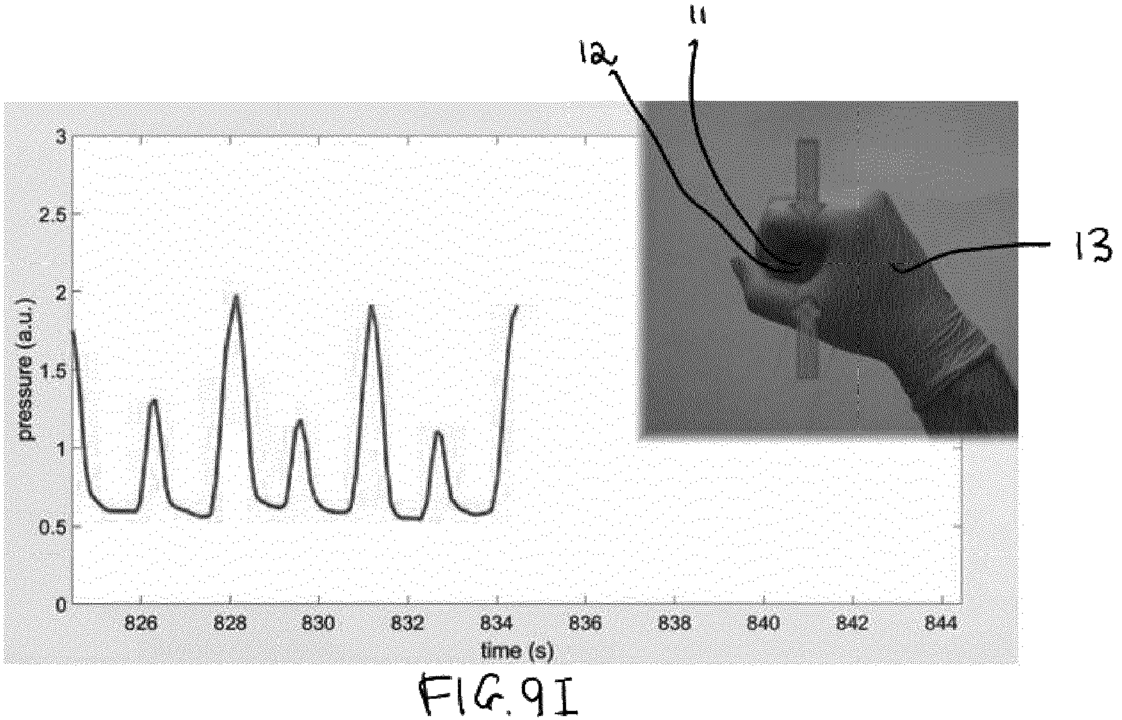
FIG. 9I shows resistance data collected using the device of FIG. 9A.

When a user 13 squeezes the device 11, the silicone ball 12 and the stretchable electronic device 1 are configured to be compressed. When the user 13 reduces the amount of squeezing force on the device 11, or stops squeezing the device 11 altogether, the silicone ball 12 and the stretchable electronic device 1 are configured to expand or return to a relaxed/released position. This is shown sequentially in FIGS. 9D-F. In FIG. 9D the user 13 holds the device 11. In FIG. 9E the user 13 softly grips the device 11. In FIG. 9F the user 13 tightly grips the device 11. FIGS. 9G and 9H show the resistance change corresponding to various squeezing rates and pressure strengths of a user 13 squeezing the device 11. The magnitude of each of the peaks in FIGS. 9G and 9H corresponds with how tightly the device 11 is squeezed/gripped by the user 13. FIG. 9I shows pressure change corresponding to various squeezes of the device 11 by a user 13. Each of the peaks in FIG. 9I corresponds with how tightly the device 11 is squeezed/gripper by the user 13.

Advantageously, the device 11 may provide for the measurement of changes in resistance to reflect changes in pressure and the amount of pressure applied to the device 11 by a user 13. For example, variations of squeeze-force with time could be used to monitor the rehabilitation of patients with hand injuries.

Figure 10:
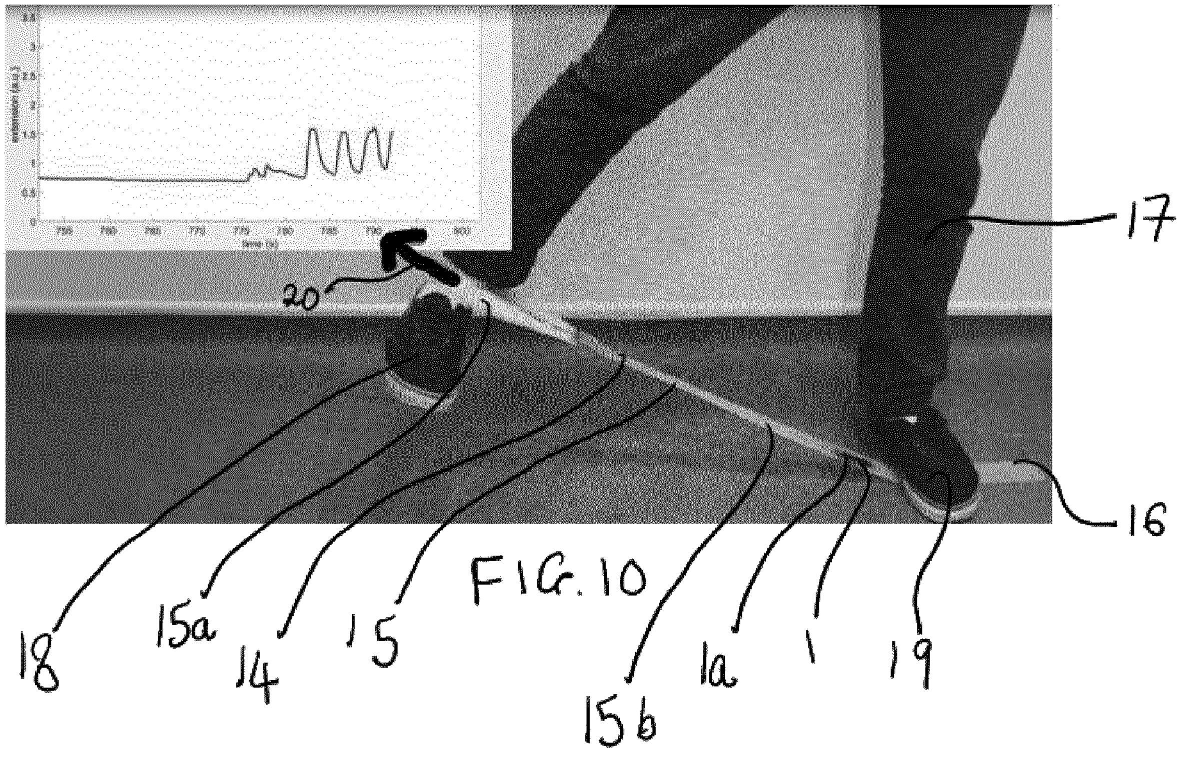
FIG. 10 shows a device for rehabilitation.

As shown in FIG. 10, the stretchable electronic device 1 may be part of a device 14 for rehabilitation. The device 14 comprises a silicone strap 15, and the stretchable electronic device 1 is attached to or integrally formed with the silicone strap 15. The silicone strap 15 has a first portion 15*a* and a second portion 15*b* and is made from polydimethylsiloxane (PDMS). Though, it is envisaged that any other silicone material may be used).

The first portion 15*a* of the silicone strap 15 comprises a loop for receiving part of a limb. In the example shown in FIG. 10, the first portion 15*a* of the silicone strap 15 is configured to receive a first foot 18 of a user 17. Though, it is envisaged that the first portion 15*a* of the silicone strap 15 may be configured to receive another body part, such as an ankle, leg, hand, wrist or arm. The second portion 15*b* of the silicone strap 15 is straight and the stretchable electronic device 1 is attached to or integrally formed with the second portion 15*b* of the silicone strap 15, as shown in FIG. 10.

The silicone strap 15 is configured to stretch when a tensile force 20 is applied thereto, and the silicone strap 15 is configured to contract or return to a relaxed/released state/position when the tensile force 20 is removed and/or decreased in magnitude. For example, to use the device 14, a user 17 may place a first foot 18 through the first portion 15*a* of the silicone strap 15*b* and may stand on an end 16 of the second portion 15*b* of the silicone strap 15 with their second foot 19. They may then cyclically apply a tensile force 20 to the silicone strap 15 by repeatedly moving their first foot 18 first away from and then back towards their second foot 19, as shown in FIG. 10, where the user 17 is shown moving their first foot 18 away from their second foot 19. FIG. 10 also shows data of extension against time for a user 17 using the device 14. The peaks correspond to maximum values of the tensile force 20. Such data may be useful in patient rehabilitation.

Figure 11A:
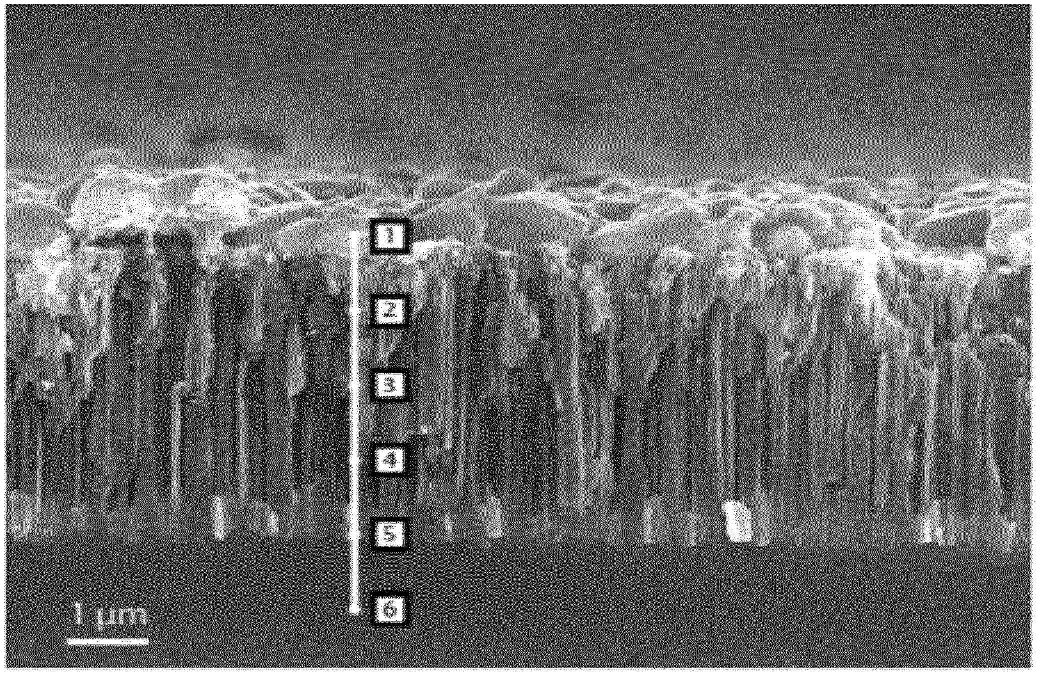
FIG. 11A shows an electron micrograph of a copper-p-type-silicon interface.
Figure 19:
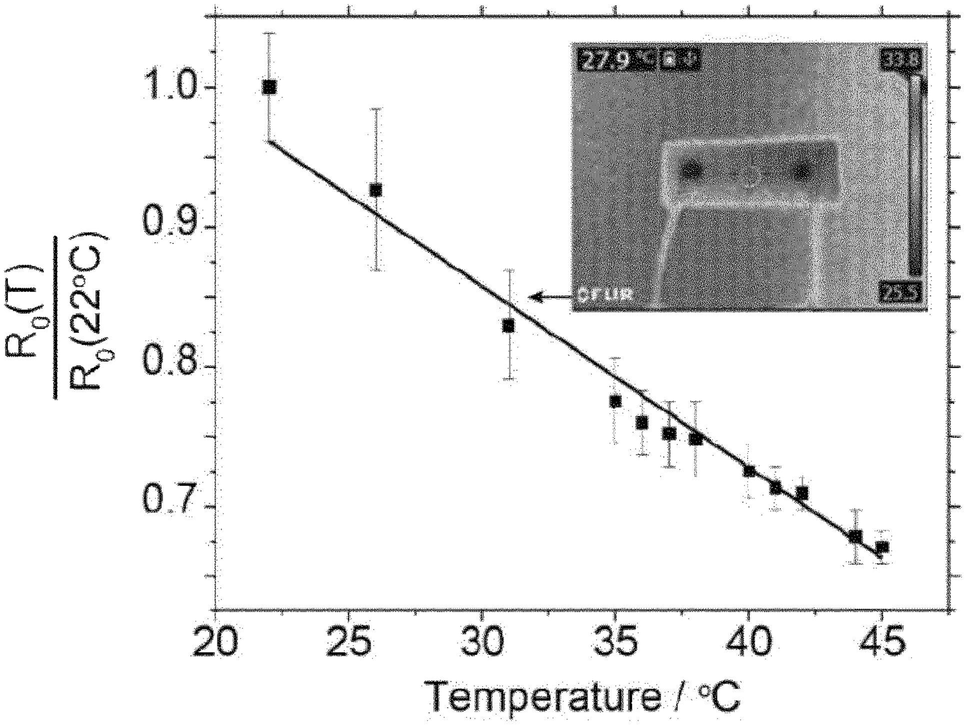
FIG. 19 shows the resistance of a CB-PDMS layered composite with copper-p-type-silicon contacts as a function of temperature.

The advantageous properties and performance of exemplary such components and stretchable electronic devices as described herein shall now be discussed further, with reference to the experimental data shown in FIG. 11A through to FIG. 19.

FIG. 11A shows an electron micrograph of an exemplary copper-p-type-silicon interface with a silver deposition time of 2 minutes. The numbers indicate the location of each spectra acquired by energy dispersive X-ray (EDX) analysis. Each measurement was taken 1 μm apart.

Figure 11B:
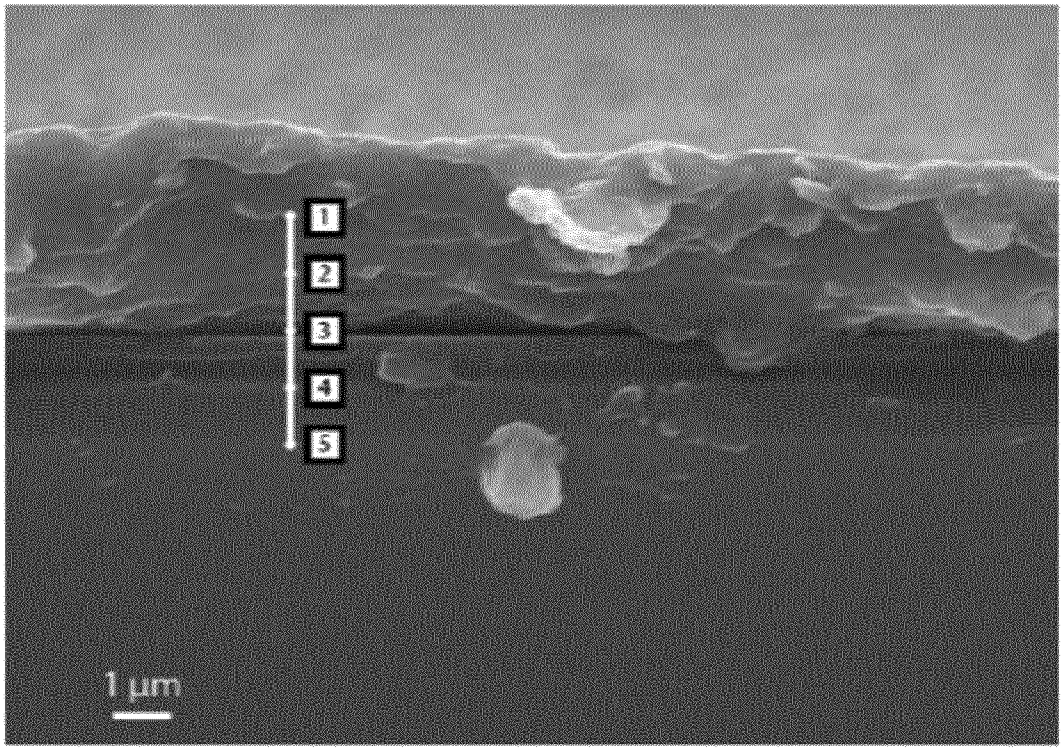
FIG. 11B shows an electron micrograph of an unetched copper-silicon interface.

FIG. 11B shows an electron micrograph of an exemplary unetched copper-silicon interface. The numbers indicate the location of each spectra acquired by EDX analysis. Each measurement was taken 1 μm apart.

Figure 11C:
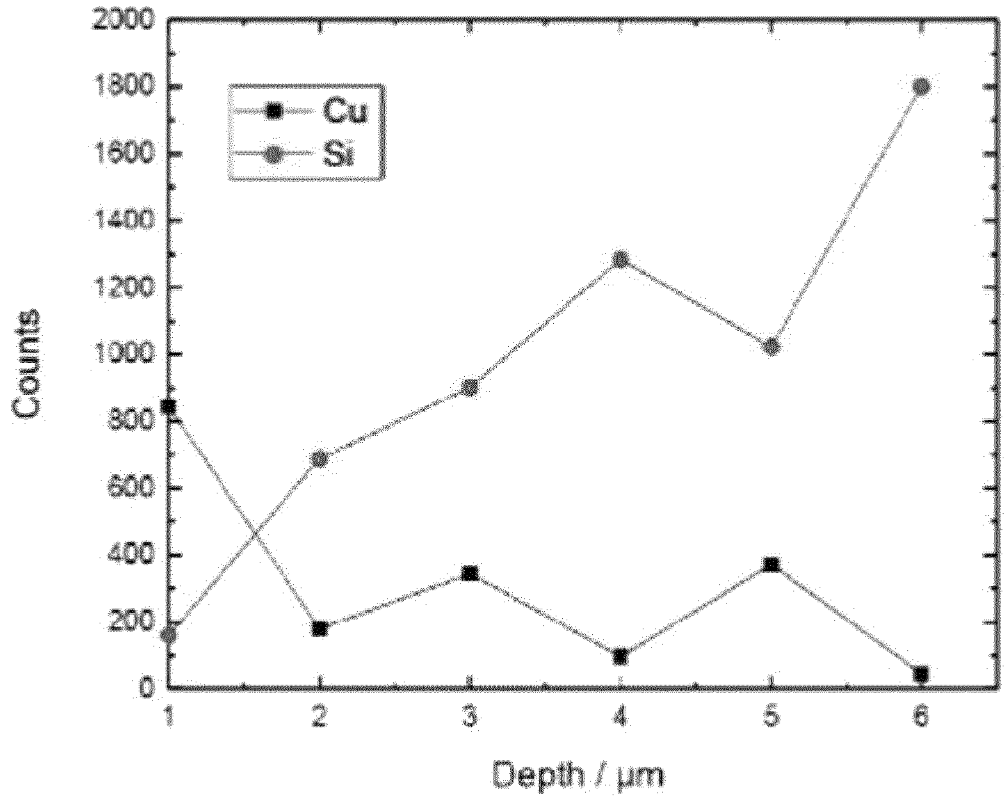
FIG. 11C shows energy dispersive X-ray (EDX) spectra for copper and silicon taken from the cross-section of electroplated p-type-silicon shown in FIG. 11A.

FIG. 11C shows EDX spectra for copper and silicon taken from the cross-section of the exemplary electroplated p-type-silicon shown in FIG. 11A.

Figure 11D:
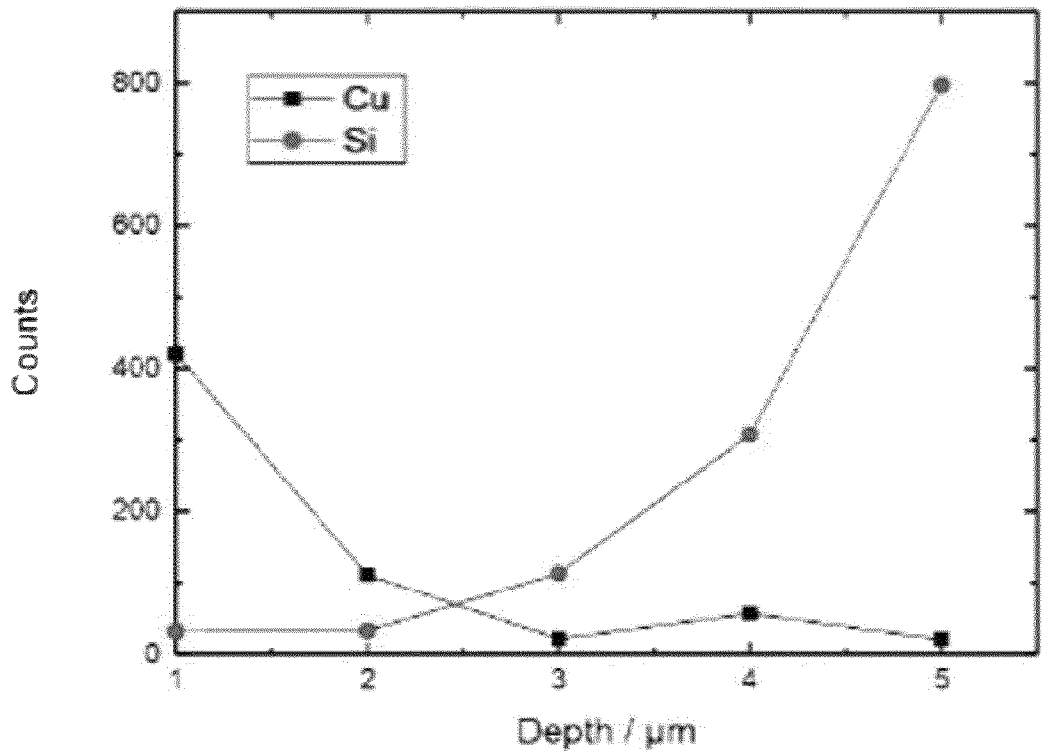
FIG. 11D shows EDX spectra for copper and silicon from the cross-section of electroplated unetched silicon shown in FIG. 11B.

FIG. 11D shows EDX spectra for copper and silicon from the cross-section of exemplary electroplated unetched silicon shown in FIG. 11B. Intensity values for copper and silicon were calculated using the peaks at 0.79 keV for copper and at 1.74 keV for silicon.

Figure 12A:
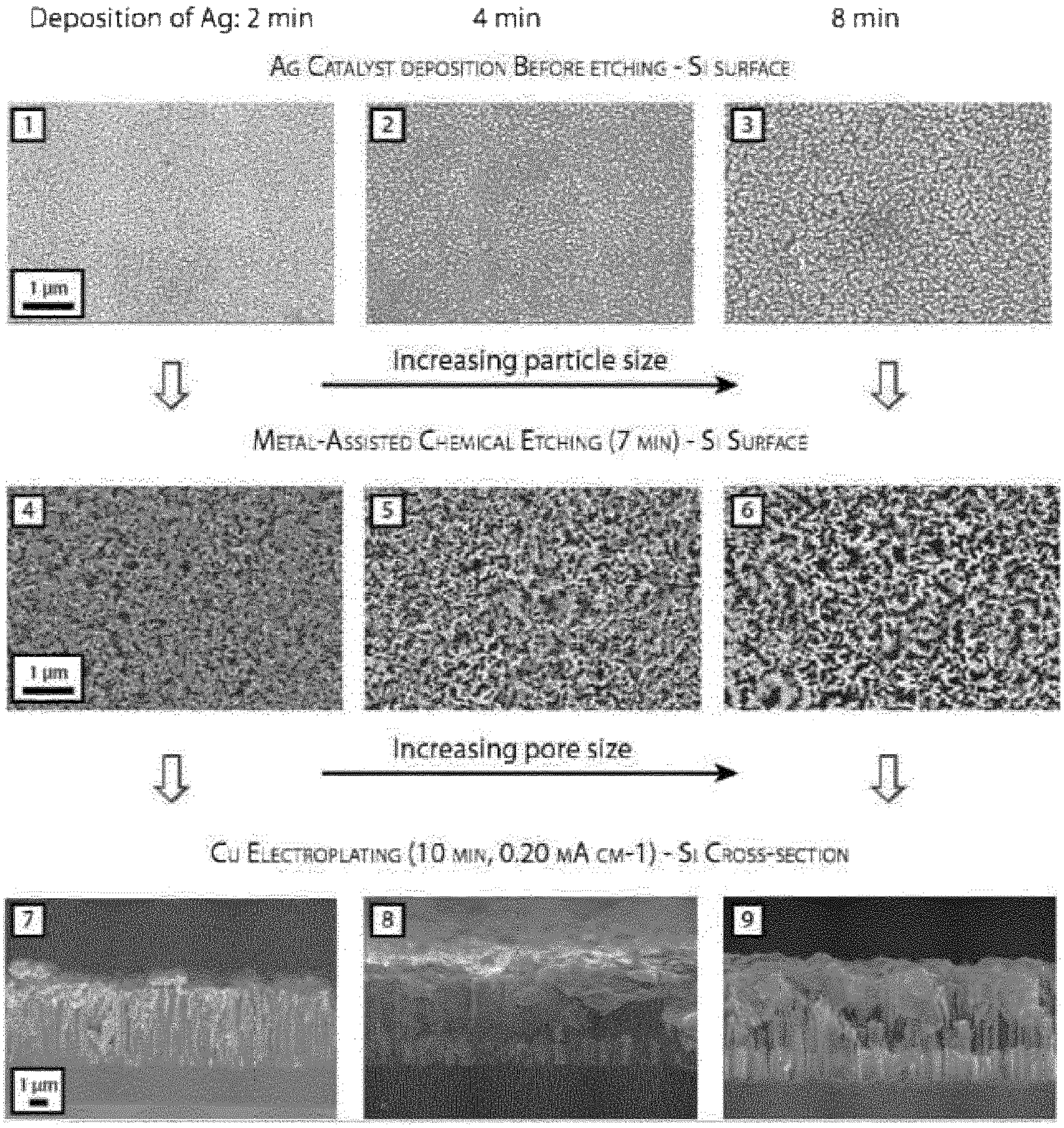
FIG. 12A shows electron micrographs of the surfaces of various silicon wafers and p-type silicon samples.

Views 1, 2 and 3 in FIG. 12A show electron micrographs of the surface of exemplary silicon wafers after depositing a silver catalyst (deposition times of 2 minutes, 4 minutes and 8 minutes for views 1, 2 and 3 respectively) with increasing particle size.

Views 4, 5 and 6 in FIG. 12A show electron micrographs of the surface of p-type-silicon with increasing silver catalyst size after etching which produced an exemplary silicon surface with larger pores.

Views 7, 8 and 9 of FIG. 12A show electron micrographs of p-type-silicon with varying pore sizes after copper electroplating showing the interface of copper and p-type-silicon. The copper layer was not deposited with an even thickness throughout the cross-section of the p-type-silicon, likely due to the limitation in mass transfer during electroplating.

Figure 12B:
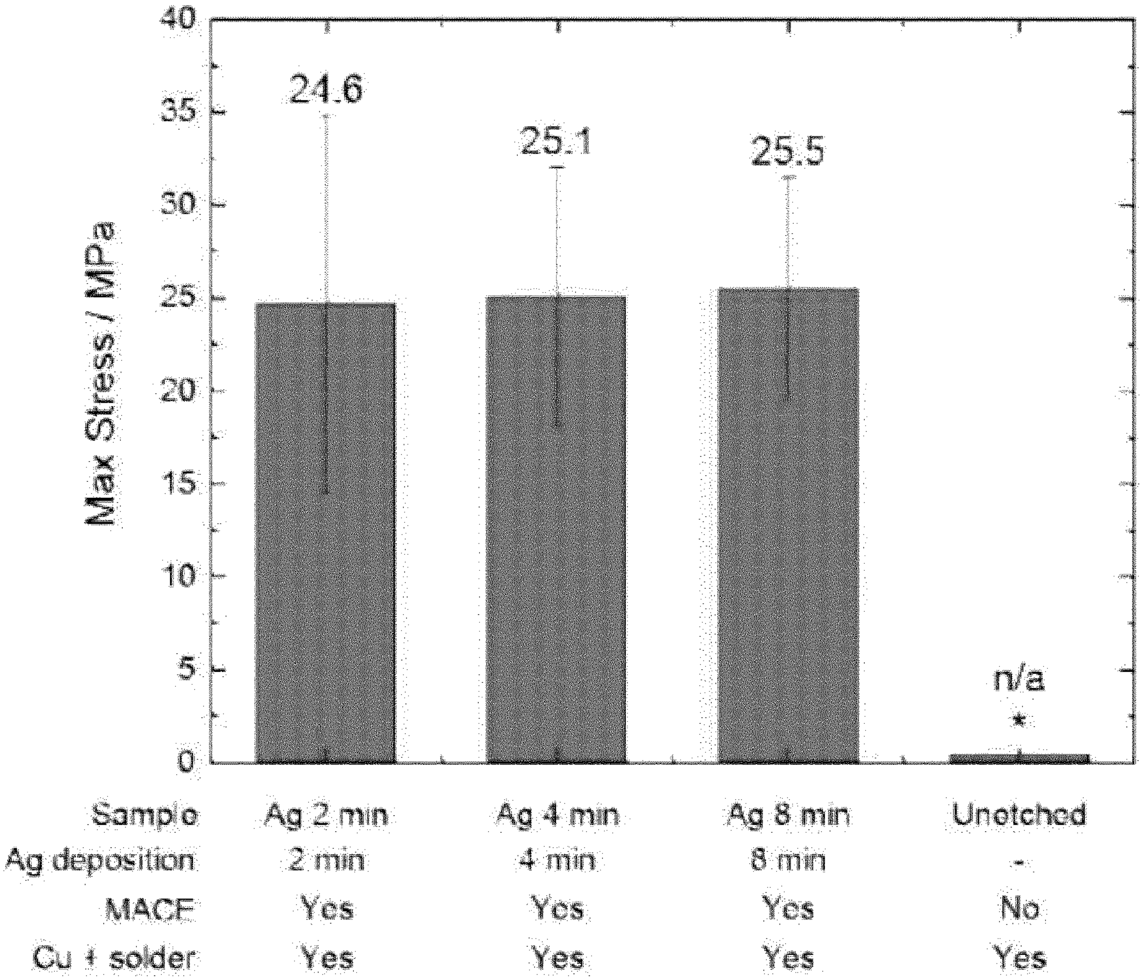
FIG. 12B shows maximum stress values for copper-p-type-silicon samples experimentally pulled to failure.

FIG. 12B shows maximum stress values for exemplary copper-p-type-silicon samples pulled to failure after a 4 mm thick multicore copper wire was soldered on the electroplated surface of p-type-silicon samples of varying pore sizes and flat, unetched silicon. The "*" in FIG. 12B represents that the maximum stress=n/a—unable to perform test, as the copper film delaminated during soldering and handling.

Figure 12C:
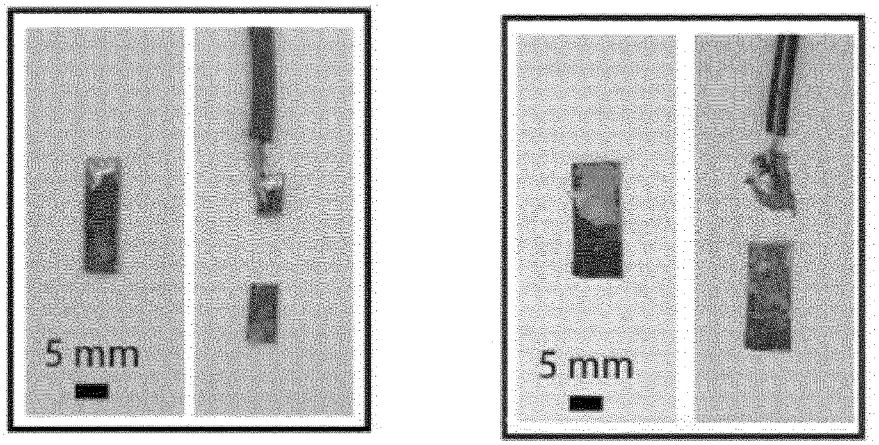
FIG. 12C shows representative photographs of the samples tested in FIG. 12B.

Views 1 (top) and 2 (bottom) in FIG. 12C show representative photographs of the samples tested in FIG. 12B showing the wafer before soldering the 4 mm multicore copper wire (view 1) and the wafer breaking before the soldered connection (view 1), and showing the unetched silicon wafer just after copper electroplating (view 2) and showing the copper film detaching from the surface of unetched silicon during soldering (view 2).

Figure 13:
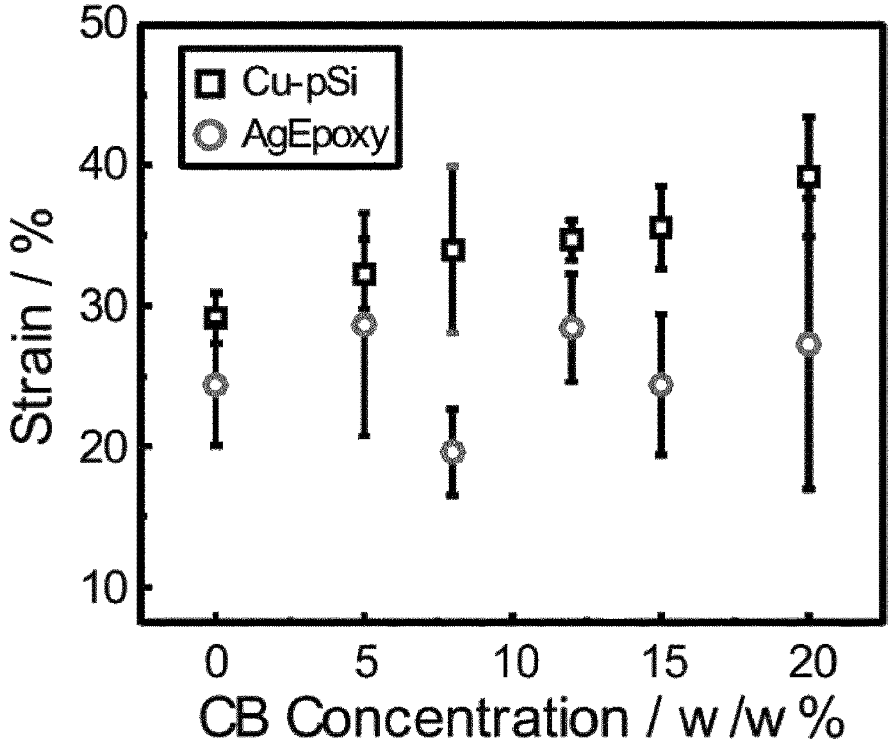
FIG. 13 shows the dependence of maximum strain at failure of copper-p-type-silicon and silver-epoxy contacts in relation to carbon-black filler concentrations in a CB-PDMS layer.

FIG. 13 shows the dependence of maximum strain at failure of copper-p-type-silicon and silver-epoxy contacts in relation to carbon-black filler concentrations (n=5) in an exemplary CB-PDMS layer.

Figure 14:
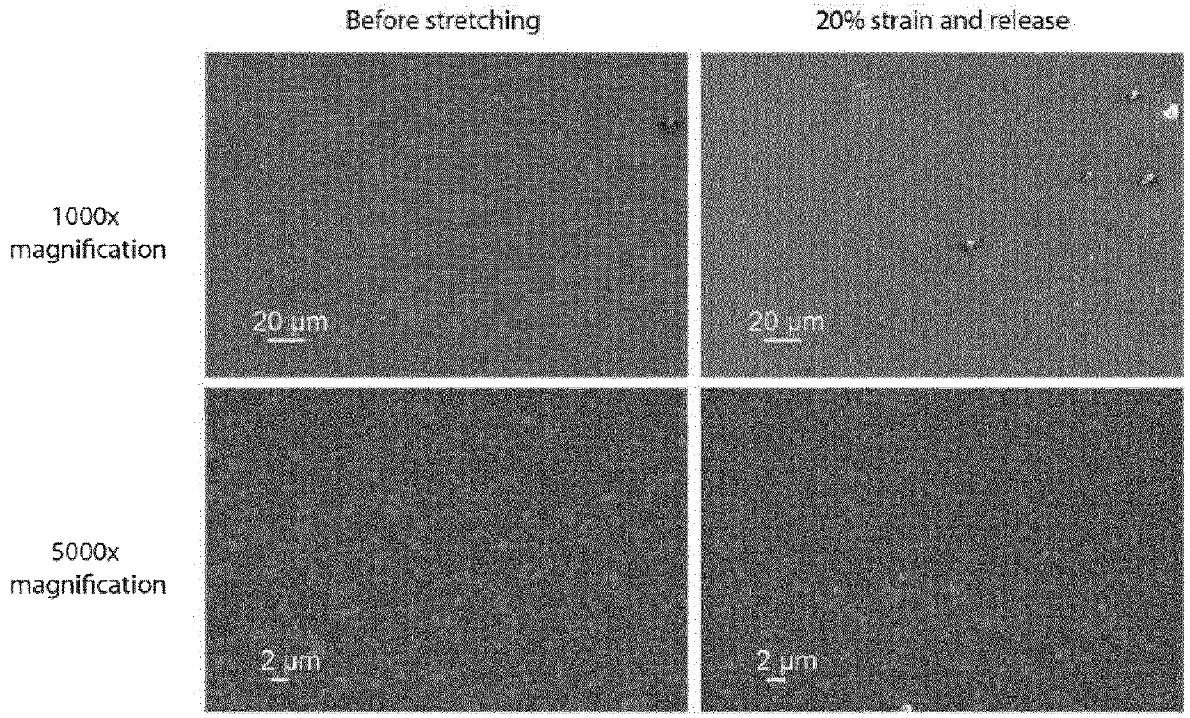
FIG. 14 shows scanning electron microscope (SEM) micrographs for the surface of a CB-PDMS sample before and after stretching.

FIG. 14 shows scanning electron microscope (SEM) micrographs for 12% CB-PDMS surface before and after stretching to 20% strain at 1000× and 5000× magnification.

Figure 15:
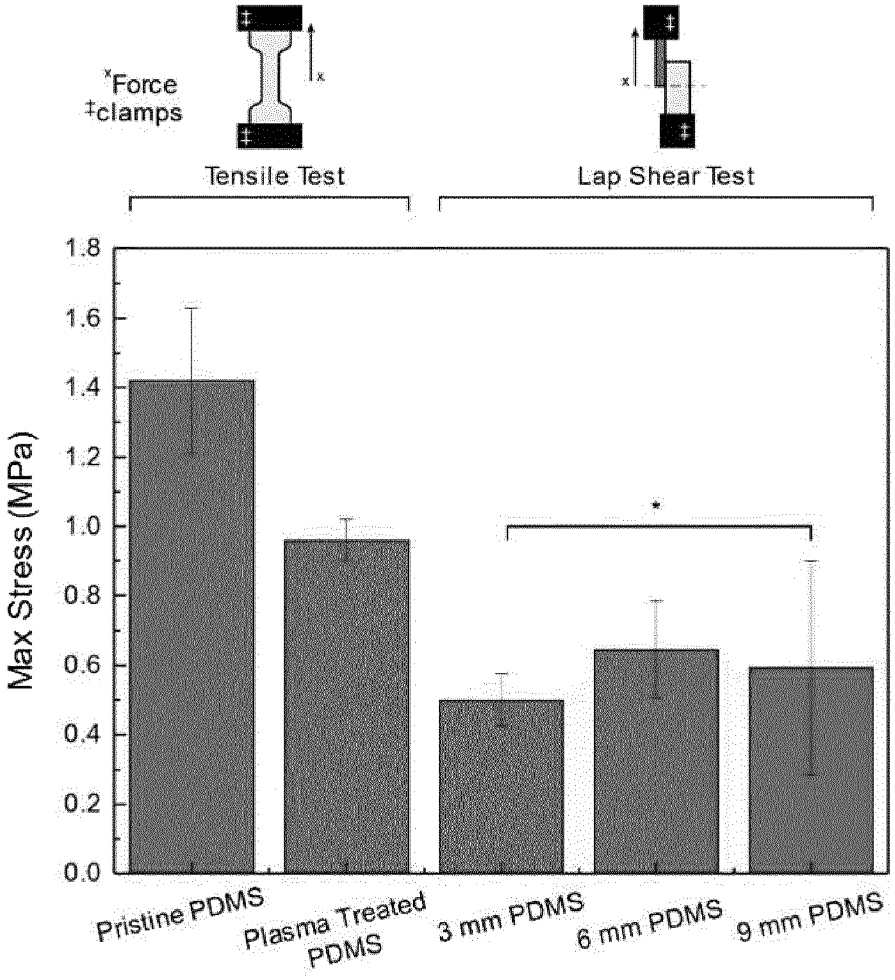
FIG. 15 shows the results from maximum stress experiments performed on different PDMS samples.

FIG. 15 shows the results from maximum stress experiments using 3 mm pristine PDMS and plasma-treated PDMS (unmasked) dog-bone samples, and samples with copper-p-type-silicon contacts prepared on PDMS substrates with 3, 6 and 9 mm thickness. No difference was observed in the values of maximum stress to failure for each thickness indicating that the fracture mechanism is a surface phenomenon only.

Figure 16A:
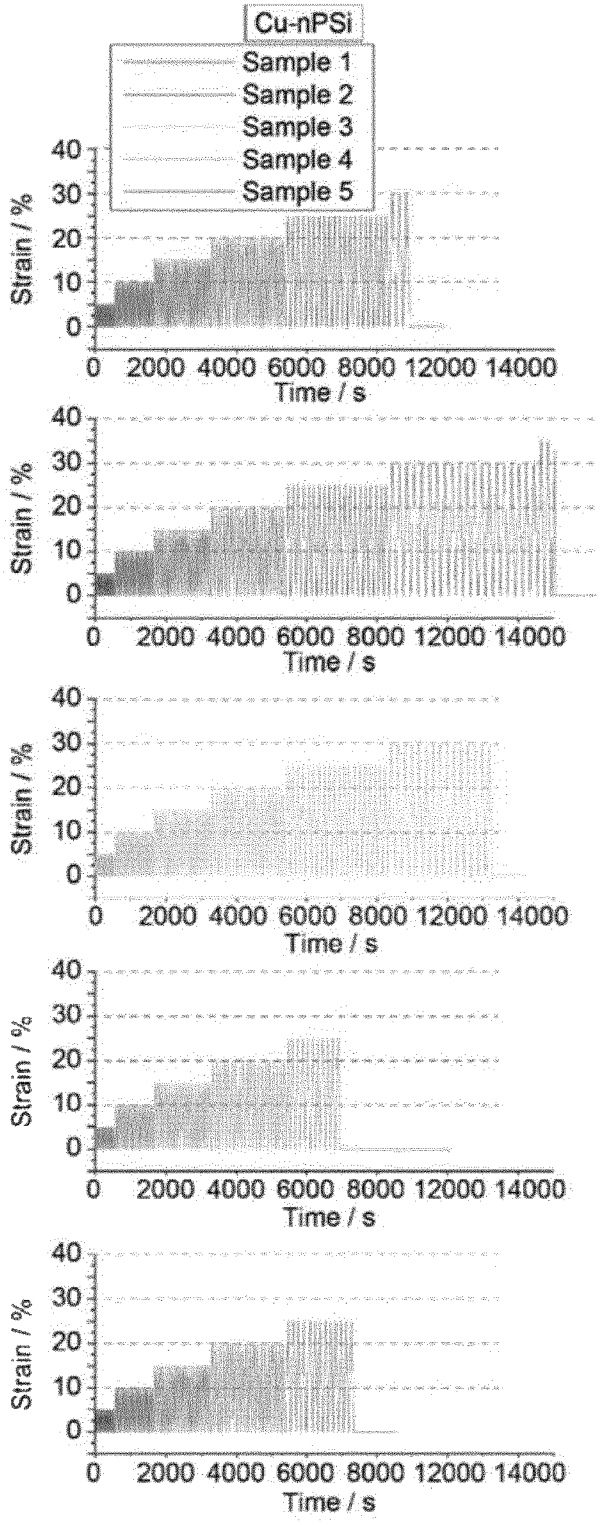
FIG. 16A shows strain values for copper-p-type-silicon contact samples during cyclic stretching.

FIG. 16A shows strain values for exemplary copper-p-type-silicon contact samples during cyclic stretching with increasing strain levels until failure, showing samples failing on average at 30%. The data shows that some samples were able to withstand strains of up to 35% before failure of CB-PDMS.

Figure 16B:
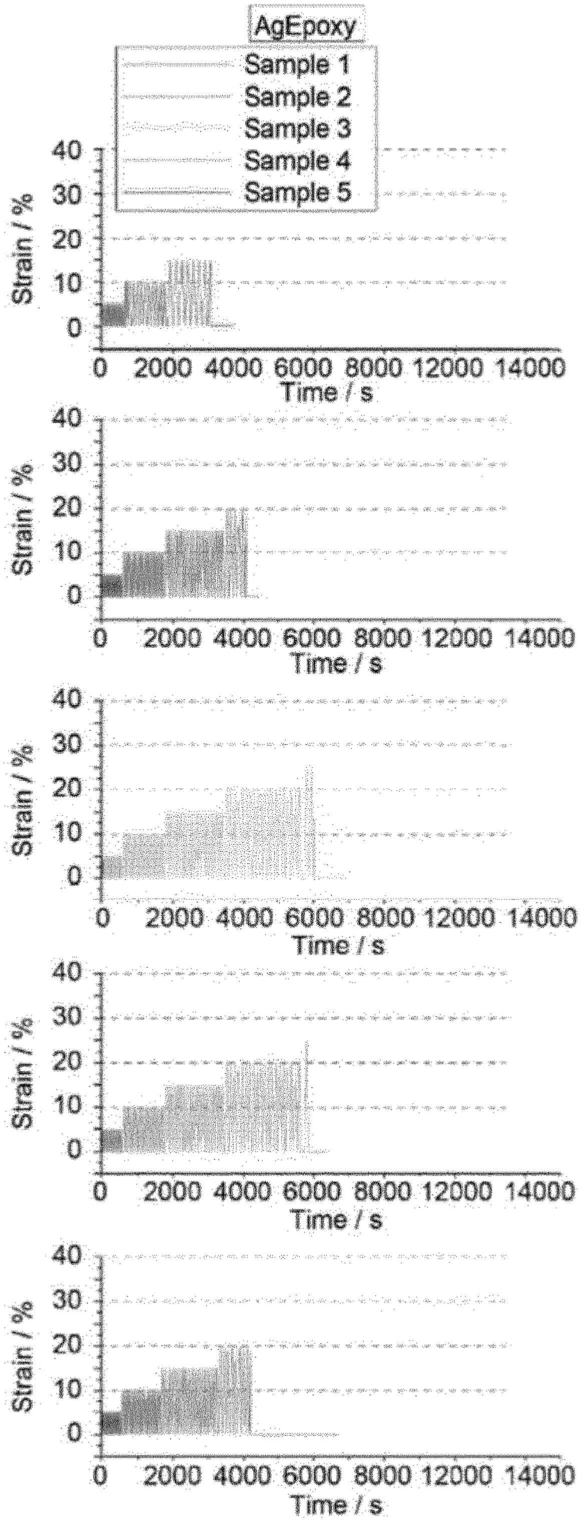
FIG. 16B shows strain values for silver-Epoxy contacts during cyclic stretching.

FIG. 16B shows strain values for exemplary silver-epoxy contacts during cyclic stretching at incremental strain levels starting from 5% and increasing by 5% every 20 cycles until failure.

Figure 17A:
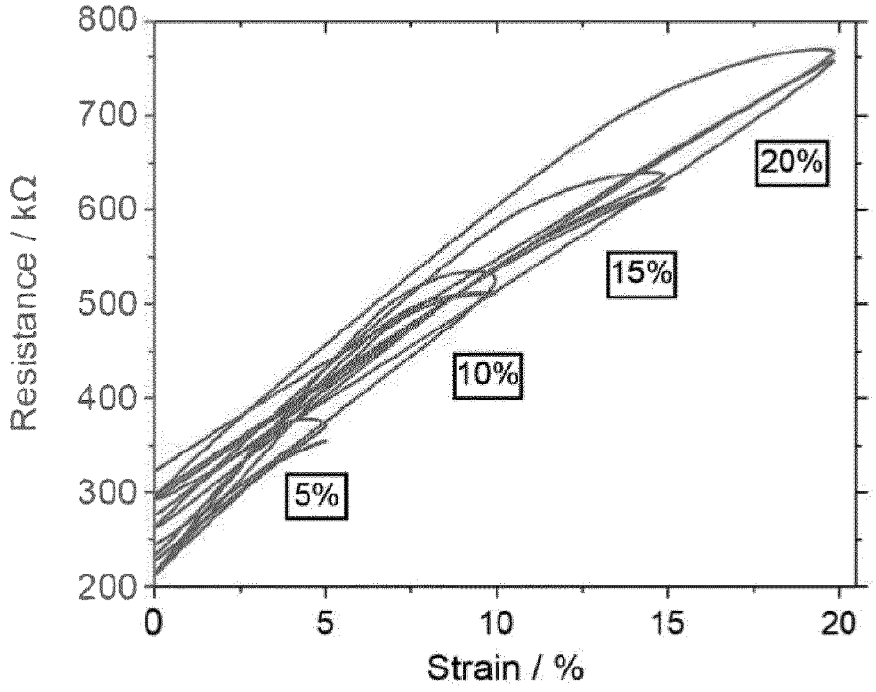
FIG. 17A shows representative curves for electrical hysteresis due to previous loading demonstrated on a CB-PDMS layered composite.
Figure 17B:
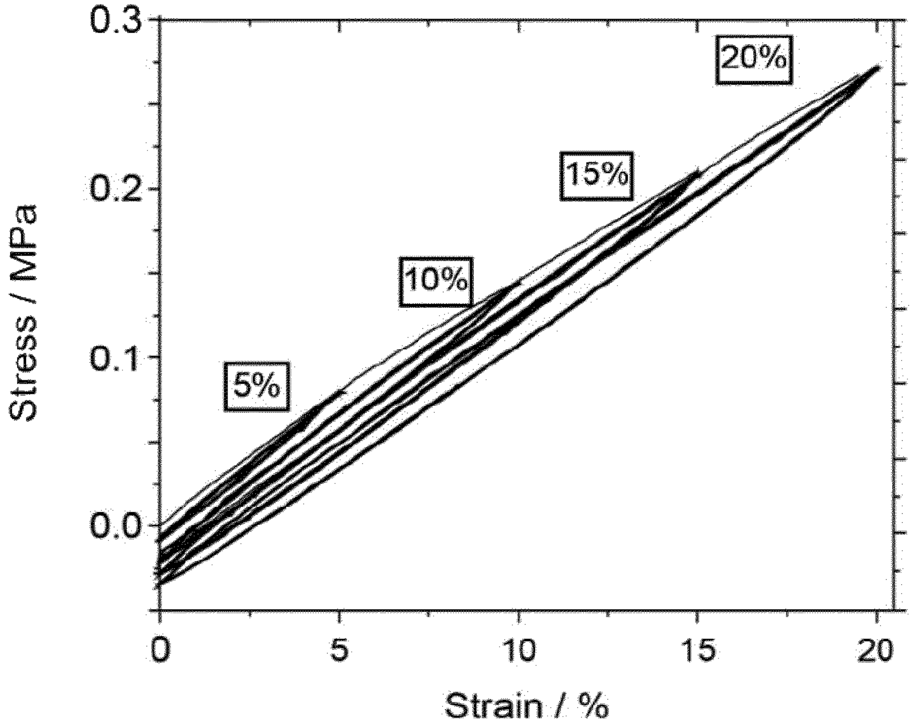
FIG. 17B shows mechanical hysteresis during cyclic stretching tests.

FIG. 17A shows representative curves for electrical hysteresis due to previous loading demonstrated on an exemplary 12% CB-PDMS layered composite. FIG. 17B shows mechanical hysteresis during cyclic stretching tests.

Figure 18:
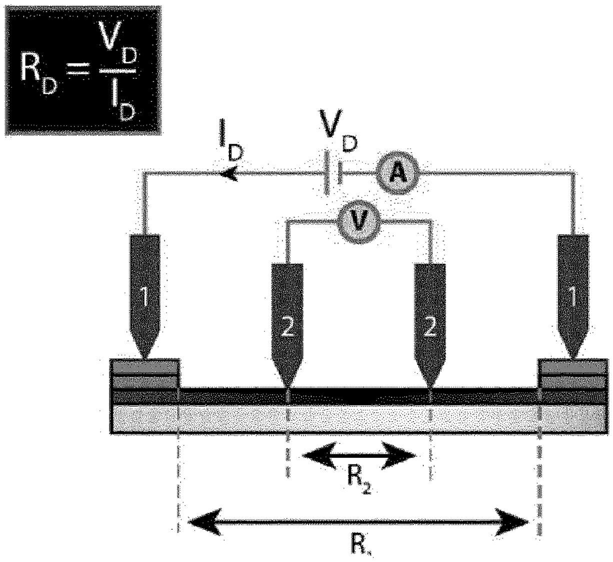
FIG. 18 shows a schematic view of a four-probe measurement setup to determine the change of contact resistance at different strain levels.

FIG. 18 shows a schematic view of a four-probe measurement setup to determine the change of contact resistance at different strain levels. The table in FIG. 18 shows the derivation of contact resistance contribution for strain levels of 0%, 10% and 25% (n=3).

FIG. 19 shows the resistance of an exemplary 12% CB-PDMS layered composite with copper-p-type-silicon contacts as a function of temperature, normalised to resistance at 22° C.

Various modifications may be made to the described embodiment(s) without departing from the scope of the invention as defined by the accompanying claims.

The invention claimed is:

1. A method of manufacturing a component for a stretchable electronic device, comprising:

providing a silicon wafer layer comprising a first surface and a second surface, wherein at least a portion of the first surface of the silicon wafer layer is nanoporous;

applying a layer of a conductive metal onto the nanoporous portion of the first surface of the silicon wafer layer;

providing a stretchable silicone substrate layer having a first surface and a second surface; and plasma bonding at least a portion of the second surface of the silicon wafer layer to at least a portion of the first surface of the stretchable silicone substrate layer, wherein the silicon wafer layer, conductive metal layer and stretchable silicon substrate layer have reliable interfacial adhesion, and where the adhesion between each of the layers is configured to catastrophically fail when a stress or strain level is exceeded.

2. The method as claimed in claim 1, wherein the method further comprises etching at least a portion of the first surface of the silicon wafer layer to create the nanoporous portion before the step of attaching the layer of a conductive metal onto the nanoporous portion of the first surface of the silicon wafer layer.

3. The method as claimed in claim 2, wherein the etching step comprises metal-assisted chemical etching.

4. The method as claimed in claim 1, wherein the conductive metal comprises one or more of copper, gold, nickel, cadmium, rhodium, platinum, silver and zinc.

5. The method as claimed in claim 1, wherein the step of attaching a layer of a conductive metal onto the nanoporous portion of the first surface of the silicon wafer layer comprises electroplating.

6. The method as claimed in claim 1, wherein at least a portion of the stretchable silicone substrate comprises a plurality of conductive particle fillers and/or one or more conductive liquids dispersed in a silicone polymer matrix.

7. The method as claimed in claim 1, wherein the stretchable silicone substrate comprises a first layer and a second layer, the first layer of the stretchable silicone substrate comprising the first surface of the stretchable silicone substrate, and the second layer of the stretchable silicone substrate comprising the second surface of the stretchable silicone substrate, wherein the first layer of the stretchable silicone substrate comprises a plurality of conductive particle fillers and/or one or more conductive liquids dispersed in a silicone polymer matrix.

8. The method as claimed in claim 7, wherein the first layer of the stretchable silicone substrate comprises carbon black-filled polydimethylsiloxane (CB-PDMS) and the second layer of the stretchable silicone substrate comprises polydimethylsiloxane (PDMS).

9. The method as claimed in claim 8, wherein the carbon black has a concentration of between 5% to 20% in the polydimethylsiloxane (PDMS) in the first layer of the stretchable silicone substrate.

10. The method as claimed in claim 7, wherein the second layer of the stretchable silicone substrate has a thickness that is greater than a thickness of the first layer of the stretchable silicone substrate.

11. The method as claimed in claim 7, wherein the step of providing a stretchable silicone substrate comprises printing the first layer of the stretchable silicone substrate on top of at least a portion of the second layer of the stretchable silicone substrate, and subsequently curing the first layer of the stretchable silicone substrate and the second layer of the stretchable silicone substrate.

12. The method as claimed in claim 11, wherein the step of curing the first layer of the stretchable silicone substrate and the second layer of the stretchable silicone substrate comprises a curing time of less than or equal to one hour and/or a curing temperature of less than or equal to 150 degrees centigrade.

13. The method as claimed in claim 1, further comprising soldering one or more electronic components onto the layer of a conductive metal.

14. The method as claimed in claim 13, wherein the step of soldering comprises tin soldering.

15. The method as claimed in claim 1, wherein the step of plasma bonding at least a portion of the second surface of the silicon wafer layer to at least a portion of the first surface of the stretchable silicone substrate comprises treating at least a portion of the second surface of the silicon wafer layer and at least a portion of the first surface of the stretchable silicone substrate in 100% 02 plasma for an operating time of approximately 35 seconds.

16. The method as claimed in claim 15, wherein the step of plasma bonding at least a portion of the second surface of the silicon wafer layer to at least a portion of the first surface of the stretchable silicone substrate further comprises providing conformal contact between at least a portion of the second surface of the silicon wafer layer and at least a portion of the first surface of the stretchable silicone substrate and applying pressure to at least a portion of the second surface of the silicon wafer layer and at least a portion of the first surface of the stretchable silicone substrate for approximately 30 seconds.

17. The method as claimed in claim 1, wherein the step of plasma bonding at least a portion of the second surface of the silicon wafer layer to at least a portion of the first surface of the stretchable silicone substrate comprises providing a mask to the first surface of the stretchable silicone substrate such that only one or more predetermined areas of the first surface of the stretchable silicone substrate are plasma bonded to at least a portion of the second surface of the silicon wafer layer.

18. A component for a stretchable electronic device, the component comprising:

a silicon wafer layer comprising a first surface and a second surface, wherein at least a portion of the first surface of the silicon wafer layer is nanoporous;

a conductive metal layer applied to the nanoporous portion of the first surface of the silicon wafer layer; and a stretchable silicone substrate layer having a first surface and a second surface, wherein at least a portion of the first surface of the stretchable silicone substrate layer is covalently bonded to at least a portion of the second surface of the silicon wafer layer, wherein the silicon wafer layer, conductive metal layer and stretchable silicon substrate layer have reliable interfacial adhesion, where the adhesion between each of the layers is configured to catastrophically fail when a stress or strain level is exceeded.

19. A stretchable electronic device comprising a component as claimed in claim 18, and further comprising one or more electronic components soldered to the conductive metal layer.

20. A device for measuring chest expansion and deformation rate, comprising a stretchable electronic device as claimed in claim 19, and a silicone chest strap, wherein at least a portion of the stretchable silicone substrate layer is attached to or integrally formed with the silicone chest strap.

21. A device for rehabilitation, comprising a stretchable electronic device as claimed in claim 19, and a silicone ball, wherein the stretchable electronic device is fully embedded in the silicone ball.

22. A device for rehabilitation, comprising a stretchable electronic device as claimed in claim 19, and a silicone strap, wherein at least a portion of the stretchable silicone substrate layer is attached to or integrally formed with the silicone strap.

23. A method of manufacturing a component for a stretchable electronic device, comprising:

providing a silicon wafer comprising a first surface and a second surface;

applying a layer of a conductive metal onto at least a portion of the first surface of the silicon wafer;

providing a stretchable silicone substrate having a first surface and a second surface; and plasma bonding at least a portion of the second surface of the silicon wafer to at least a portion of the first surface of the stretchable silicone substrate, wherein the step of plasma bonding at least a portion of the second surface of the silicon wafer to at least a portion of the first surface of the stretchable silicone substrate further comprises providing a mask to the first surface of the stretchable silicone substrate such that only one or more predetermined areas of the first surface of the stretchable silicone substrate are plasma bonded to at least a portion of the second surface of the silicon wafer.

* * * * *